(12) United States Patent
Parikh

(10) Patent No.: US 8,685,393 B2
(45) Date of Patent: Apr. 1, 2014

(54) METHODS AND COMPOSITIONS FOR THE TREATMENT AND DIAGNOSIS OF SYSTEMIC ANTHRAX INFECTION

(75) Inventor: Samir M. Parikh, Roslindale, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 183 days.

(21) Appl. No.: 12/934,430

(22) PCT Filed: Mar. 23, 2009

(86) PCT No.: PCT/US2009/001797
§ 371 (c)(1),
(2), (4) Date: Jan. 6, 2011

(87) PCT Pub. No.: WO2010/011242
PCT Pub. Date: Jan. 28, 2010

(65) Prior Publication Data
US 2011/0110939 A1    May 12, 2011

Related U.S. Application Data

(60) Provisional application No. 61/070,581, filed on Mar. 24, 2008.

(51) Int. Cl.
*A61K 39/00*    (2006.01)
*A61K 39/395*   (2006.01)

(52) U.S. Cl.
USPC ..................................... 424/130.1; 424/133.1

(58) Field of Classification Search
None
See application file for complete search history.

(56) References Cited

U.S. PATENT DOCUMENTS

| 7,521,053 B2 * | 4/2009 | Oliner .......................... 424/155.1 |
| 2003/0143636 A1 * | 7/2003 | Simonson et al. ............. 435/7.9 |
| 2005/0272055 A1 | 12/2005 | Das et al. |

FOREIGN PATENT DOCUMENTS

WO    WO 2007/033216    *    3/2007

OTHER PUBLICATIONS

Depeille et al., "Anthrax lethal toxin inhibits growth of and vascular endothelial growth factor release from endothelial cells expressing the human herpes virus 8 viral G protein coupled receptor," *Clin. Cancer Res.* 13(19):5926-5934, 2007.

Kuo et al., "Anthrax toxin-induced shock in rats is associated with pulmonary edema and hemorrhage," *Microb Pathog.* 44:467-472, 2008.

Lim et al., "An anthrax lethal factor-neutralizing monoclonal antibody protects rats before and after challenge with anthrax toxin," *Infect Immun.* 73(10):6547-6551, 2005.

Written Opinion and International Search Report for International Application No. PCT/US2009/001797, mailed Mar. 16, 2010 (8 pages).

* cited by examiner

*Primary Examiner* — Albert Navarro
(74) *Attorney, Agent, or Firm* — Clark & Elbing LLP; Kristina Bieker-Brady

(57) ABSTRACT

The present invention features methods and kits that utilize Ang-2 antagonists for the treatment, inhibition, and prevention of a systemic anthrax infection. The invention described herein also features methods for the diagnosis of a systemic anthrax infection by detecting elevated levels of Ang-2 in the serum of a subject.

15 Claims, 16 Drawing Sheets

Figure 1

Ang-2 time course in Baboon Anthrax (6e9)

Figure 2

Ang-2 time course in Baboon Anthrax (1e9)

Figure 8

Time series data: treated vs. untreated

- Sterne + Xigris
- 6e9 Sterne only
- 5e6 Sterne only

Time (min rel to anthrax infusion)

Angpt-2 (pg/ml)

Figure 12

```
Met Thr Val Phe Leu Ser Phe Ala Phe Leu Ala Ala Ile Leu Thr His      16
Ile Gly Cys Ser Asn Gln Arg Arg Ser Pro Glu Asn Ser Gly Arg Arg      32
Tyr Asn Arg Ile Gln His Gly Gln Cys Ala Tyr Thr Phe Ile Leu Pro      48
Glu His Asp Gly Asn Cys Arg Glu Ser Thr Thr Asp Gln Tyr Asn Thr      64
Asn Ala Leu Gln Arg Asp Ala Pro His Val Glu Pro Asp Phe Ser Ser      80
Gln Lys Leu Gln His Leu Glu His Val Met Glu Asn Tyr Thr Gln Trp      96
Leu Gln Lys Leu Glu Asn Tyr Ile Val Glu Asn Met Lys Ser Glu Met     112
Ala Gln Ile Gln Gln Asn Ala Val Gln Asn His Thr Ala Thr Met Leu     128
Glu Ile Gly Thr Ser Leu Leu Ser Gln Thr Ala Glu Gln Thr Arg Lys     144
Leu Thr Asp Val Glu Thr Gln Val Leu Asn Gln Thr Ser Arg Leu Glu     160
Ile Gln Leu Leu Glu Asn Ser Leu Ser Thr Tyr Lys Leu Glu Lys Gln     176
Leu Leu Gln Gln Thr Asn Glu Ile Leu Lys Ile His Glu Lys Asn Ser     192
Leu Leu Glu His Lys Ile Leu Glu Met Glu Gly Lys His Lys Glu Glu     208
Leu Asp Thr Leu Lys Glu Glu Lys Glu Asn Leu Gln Gly Leu Val Thr     224
Arg Gln Thr Tyr Ile Ile Gln Glu Leu Glu Lys Gln Leu Asn Arg Ala     240
Thr Thr Asn Asn Ser Val Leu Gln Lys Gln Gln Leu Glu Leu Met Asp     256
Thr Val His Asn Leu Val Asn Leu Cys Thr Lys Glu Gly Val Leu Leu     272
Lys Gly Gly Lys Arg Glu Glu Glu Lys Pro Phe Arg Asp Cys Ala Asp     288
Val Tyr Gln Ala Gly Phe Asn Lys Ser Gly Ile Tyr Thr Ile Tyr Ile     304
Asn Asn Met Pro Glu Pro Lys Lys Val Phe Cys Asn Met Asp Val Asn     320
Gly Gly Gly Trp Thr Val Ile Gln His Arg Glu Asp Gly Ser Leu Asp     336
Phe Gln Arg Gly Trp Lys Glu Tyr Lys Met Gly Phe Gly Asn Pro Ser     352
Gly Glu Tyr Trp Leu Gly Asn Glu Phe Ile Phe Ala Ile Thr Ser Gln     368
Arg Gln Tyr Met Leu Arg Ile Glu Leu Met Asp Trp Glu Gly Asn Arg     384
Ala Tyr Ser Gln Tyr Asp Arg Phe His Ile Gly Asn Glu Lys Gln Asn     400
Tyr Arg Leu Tyr Leu Lys Gly His Thr Gly Thr Ala Gly Lys Gln Ser     416
Ser Leu Ile Leu His Gly Ala Asp Phe Ser Thr Lys Asp Ala Asp Asn     432
Asp Asn Cys Met Cys Lys Cys Ala Leu Met Leu Thr Gly Gly Trp Trp     448
Phe Asp Ala Cys Gly Pro Ser Asn Leu Asn Gly Met Phe Tyr Thr Ala     464
Gly Gln Asn His Gly Lys Leu Asn Gly Ile Lys Trp His Tyr Phe Lys     480
Gly Pro Ser Tyr Ser Leu Arg Ser Thr Thr Met Met Ile Arg Pro Leu     496
```

Figure 13

```
ggggcacact catgcattcc tgtcaagtca tcttgtgaaa ggctgcctgc ttccagcttg    60
gcttggatgt gcaaccttaa taaaactcac tgaggtctgg gagaaaatag cagatctgca   120
gcagataggg tagaggaaag ggtctagaat atgtacacgc agctgactca ggcaggctcc   180
atgctgaacg gtcacacaga gaggaaacaa taaatctcag ctactatgca ataaatatct   240
caagttttaa cgaagaaaaa catcattgca gtgaaataaa aattttaaa attttagaac    300
aaagctaaca aatggctagt tttctatgat tcttcttcaa acgctttctt tgaggggaa    360
agagtcaaac aaacaagcag ttttacctga aataaagaac tagttttaga ggtcagaaga   420
aaggagcaag ttttgcgaga ggcacggaag gagtgtgctg gcagtacaat gacagttttc   480
ctttcctttg ctttcctcgc tgccattctg actcacatag ggtgcagcaa tcagcgccga   540
agtccagaaa acagtgggag aagatataac cggattcaac atgggcaatg tgcctacact   600
ttcattcttc cagaacacga tggcaactgt cgtgagagta cgacagacca gtacaacaca   660
aacgctctgc agagagatgc tccacacgtg gaaccggatt tctcttccca gaaacttcaa   720
catctggaac atgtgatgga aaattatact cagtggctgc aaaaacttga gaattacatt   780
gtggaaaaca tgaagtcgga gatggcccag atacagcaga atgcagttca gaaccacacg   840
gctaccatgc tggagatagg aaccagcctc ctctctcaga ctgcagagca gaccagaaag   900
ctgacagatg ttgagaccca ggtactaaat caaacttctc gacttgagat acagctgctg   960
gagaattcat tatccaccta caagctagag aagcaacttc ttcaacgac aaatgaaatc   1020
ttgaagatcc atgaaaaaaa cagtttatta gaacataaaa tcttagaaat ggaaggaaaa   1080
cacaaggaag agttggacac cttaaaggaa gagaaagaga accttcaagg cttggttact   1140
cgtcaaacat atataatcca ggagctggaa aagcaattaa acagagctac caccaacaac   1200
agtgtccttc agaagcagca actggagctg atggacacag tccacaacct tgtcaatctt   1260
tgcactaaag aaggtgtttt actaagggga ggaaaagag aggaagagaa accatttaga    1320
gactgtgcag atgtatatca agctggtttt aataaaagtg gaatctacac tatttatatt   1380
aataatatgc cagaacccaa aaaggtgttt tgcaatatgg atgtcaatgg gggaggttgg   1440
actgtaatac aacatcgtga agatggaagt ctagatttcc aaagaggctg gaaggaatat   1500
aaaatgggtt ttggaaatcc ctccggtgaa tattggctgg ggaatgagtt tatttttgcc   1560
attaccagtc agaggcagta catgctaaga attgagttaa tggactggga agggaaccga   1620
gcctattcac agtatgacag attccacata ggaaatgaaa agcaaaacta taggttgtat   1680
ttaaaaggtc acactgggac agcaggaaaa cagagcagcc tgatcttaca cggtgctgat   1740
ttcagcacta aagatgctga taatgacaac tgtatgtgca atgtgccct catgttaaca    1800
ggaggatggt ggtttgatgc ttgtggcccc tccaatctaa atggaatgtt ctatactgcg   1860
ggacaaaacc atggaaaact gaatgggata aagtggcact acttcaaagg cccagttac    1920
tccttacgtt ccacaactat gatgattcga cctttagatt tttgaaagcg caatgtcaga   1980
agcgattatg aaagcaacaa agaaatccgg agaagctgcc aggtgagaaa ctgtttgaaa   2040
acttcagaag caaacaatat tgtctccctt ccagcaataa gtggtagtta tgtgaagtca   2100
ccaaggttct tgaccgtgaa tctggagccg tttgagttca agagtctc tacttggggt    2160
gacagtgctc acgtggctcg actatagaaa actccactga ctgtcgggct ttaaaagggg   2220
```

Figure 13 (cont.)

```
aagaaactgc tgagcttgct gtgcttcaaa ctactactgg accttatttt ggaactatgg   2280
tagccagatg ataaatatgg ttaatttcat gtaaaacaga aaaaaagagt gaaaaagaga   2340
atatacatga agaatagaaa caagcctgcc ataatccttt ggaaaagatg tattatacca   2400
gtgaaaaggt gttatatcta tgcaaaccta ctaacaaatt atactgttgc acaattttga   2460
taaaaattta gaacagcatt gtcctctgag ttggttaaat gttaatggat ttcagaagcc   2520
taattccagt atcatactta ctagttgatt tctgcttacc catcttcaaa tgaaaattcc   2580
attttttgtaa gccataatga actgtagtac atggacaata agtgtgtggt agaaacaaac   2640
tccattactc tgattttttga tacagttttc agaaaaagaa atgaacataa tcaagtaagg   2700
atgtatgtgg tgaaaactta ccaccccccat actatggttt tcatttactc taaaaactga   2760
ttgaatgata tataaatata tttatagcct gagtaaagtt aaaagaatgt aaaatatatc   2820
atcaagttct taaaataata tacatgcatt taatatttcc tttgatatta tacaggaaag   2880
caatattttg gagtatgtta agttgaagta aagcaagta ctctggagca gttcatttta    2940
cagtatctac ttgcatgtgt atacatacat gtaacttcat tatttttaaaa atattttttag  3000
aactccaata ctcaccctgt tatgtcttgc taatttaaat tttgctaatt aactgaaaca   3060
tgcttaccag attcacactg ttccagtgtc tataaaagaa acactttgaa gtctataaaa   3120
aataaaataa ttataaaatat cattgtacat agcatgttta tatctgcaaa aaacctaata  3180
gctaattaat ctggaatatg caacattgtc cttaattgat gcaaataaca caaatgctca   3240
aagaaatcta ctatatccct taatgaaata catcattctt catatatttc tccttcagtc   3300
cattccctta ggcaattttt aattttttaaa aattattatc aggggagaaa aattggcaaa  3360
actattatat gtaagggaaa tatatacaaa aagaaaatta atcatagtca cctgactaag   3420
aaattctgac tgctagttgc cataaataac tcaatggaaa tattcctatg ggataatgta   3480
ttttaagtga attttttgggg tgcttgaagt tactgcatta ttttatcaag aagtcttctc   3540
tgcctgtaag tgtccaaggt tatgacagta aacagttttt attaaaacat gagtcactat   3600
gggatgagaa aattgaaata aagctactgg gcctcctctc ataaaagaga cagttgttgg   3660
caaggtagca ataccagttt caaacttggt gacttgatcc actatgcctt aatggtttcc   3720
tccatttgag aaaataaagc tattcacatt gttaagaaaa atactttta aagtttacca    3780
tcaagtcttt tttatattta tgtgtctgta ttctacccct ttttgcctta caagtgatat   3840
ttgcaggtat tataccattt ttctattctt ggtggcttct tcatagcagg taagcctctc   3900
cttctaaaaa cttctcaact gttttcattt aagggaaaga aaatgagtat tttgtccttt   3960
tgtgttccta cagacacttt cttaaaccag tttttggata aagaatacta tttccaaact   4020
catattacaa aaacaaaata aaataataaa aaaagaaagc atgatattta ctgttttgtt   4080
gtctgggttt gagaaatgaa atattgtttc caattattta taataaatca gtataaaatg   4140
ttttatgatt gttatgtgta ttatgtaata cgtacatgtt tatggcaatt taacatgtgt   4200
attcttttaa ttgtttcaga ataggataat taggtattcg aattttgtct ttaaaattca   4260
tgtggtttct atgcaaagtt cttcatatca tcacaacatt atttgattta aataaaattg   4320
aaagtaatat ttgtgcaa                                                 4338
```

Figure 14

```
Met Trp Gln Ile Val Phe Phe Thr Leu Ser Cys Asp Leu Val Leu Ala   16
Ala Ala Tyr Asn Asn Phe Arg Lys Ser Met Asp Ser Ile Gly Lys Lys   32
Gln Tyr Gln Val Gln His Gly Ser Cys Ser Tyr Thr Phe Leu Leu Pro   48
Glu Met Asp Asn Cys Arg Ser Ser Ser Ser Pro Tyr Val Ser Asn Ala   64
Val Gln Arg Asp Ala Pro Leu Glu Tyr Asp Asp Ser Val Gln Arg Leu   80
Gln Val Leu Glu Asn Ile Met Glu Asn Asn Thr Gln Trp Leu Met Lys   96
Leu Glu Asn Tyr Ile Gln Asp Asn Met Lys Lys Glu Met Val Glu Ile  112
Gln Gln Asn Ala Val Gln Asn Gln Thr Ala Val Met Ile Glu Ile Gly  128
Thr Asn Leu Leu Asn Gln Thr Ala Glu Gln Thr Arg Lys Leu Thr Asp  144
Val Glu Ala Gln Val Leu Asn Gln Thr Thr Arg Leu Glu Leu Gln Leu  160
Leu Glu His Ser Leu Ser Thr Asn Lys Leu Glu Lys Gln Ile Leu Asp  176
Gln Thr Ser Glu Ile Asn Lys Leu Gln Asp Lys Asn Ser Phe Leu Glu  192
Lys Lys Val Leu Ala Met Glu Asp Lys His Ile Ile Gln Leu Gln Ser  208
Ile Lys Glu Glu Lys Asp Gln Leu Gln Val Leu Val Ser Lys Gln Asn  224
Ser Ile Ile Glu Glu Leu Glu Lys Lys Ile Val Thr Ala Thr Val Asn  240
Asn Ser Val Leu Gln Lys Gln Gln His Asp Leu Met Glu Thr Val Asn  256
Asn Leu Leu Thr Met Met Ser Thr Ser Asn Ser Ala Lys Asp Pro Thr  272
Val Ala Lys Glu Glu Gln Ile Ser Phe Arg Asp Cys Ala Glu Val Phe  288
Lys Ser Gly His Thr Thr Asn Gly Ile Tyr Thr Leu Thr Phe Pro Asn  304
Ser Thr Glu Glu Ile Lys Ala Tyr Cys Asp Met Glu Ala Gly Gly Gly  320
Gly Trp Thr Ile Ile Gln Arg Arg Glu Asp Gly Ser Val Asp Phe Gln  336
Arg Thr Trp Lys Glu Tyr Lys Val Gly Phe Gly Asn Pro Ser Gly Glu  352
Tyr Trp Leu Gly Asn Glu Phe Val Ser Gln Leu Thr Asn Gln Gln Arg  368
Tyr Val Leu Lys Ile His Leu Lys Asp Trp Glu Gly Asn Glu Ala Tyr  384
Ser Leu Tyr Glu His Phe Tyr Leu Ser Ser Glu Glu Leu Asn Tyr Arg  400
Ile His Leu Lys Gly Leu Thr Gly Thr Ala Gly Lys Ile Ser Ser Ile  416
Ser Gln Pro Gly Asn Asp Phe Ser Thr Lys Asp Gly Asp Asn Asp Lys  432
Cys Ile Cys Lys Cys Ser Gln Met Leu Thr Gly Gly Trp Trp Phe Asp  448
Ala Cys Gly Pro Ser Asn Leu Asn Gly Met Tyr Tyr Pro Gln Arg Gln  464
Asn Thr Asn Lys Phe Asn Gly Ile Lys Trp Tyr Tyr Trp Lys Gly Ser  480
Gly Tyr Ser Leu Lys Ala Thr Thr Met Met Ile Arg Pro Ala Asp Phe  496
```

Figure 15

```
tgggttggtg tttatctcct cccagccttg agggagggaa caacactgta ggatctgggg    60
agagaggaac aaaggaccgt gaaagctgct ctgtaaaagc tgacacagcc ctcccaagtg   120
agcaggactg ttcttcccac tgcaatctga cagtttactg catgcctgga gagaacacag   180
cagtaaaaac caggtttgct actggaaaaa gaggaaagag aagactttca ttgacggacc   240
cagccatggc agcgtagcag ccctgcgttt cagacggcag cagctcggga ctctggacgt   300
gtgtttgccc tcaagtttgc taagctgctg gtttattact gaagaaagaa tgtggcagat   360
tgttttcttt actctgagct gtgatcttgt cttggccgca gcctataaca actttcggaa   420
gagcatggac agcataggaa agaagcaata tcaggtccag catgggtcct gcagctacac   480
tttcctcctg ccagagatgg acaactgccg ctcttcctcc agccctacg tgtccaatgc    540
tgtgcagagg gacgcgccgc tcgaatacga tgactcggtg cagaggctgc aagtgctgga   600
gaacatcatg gaaaacaaca ctcagtggct aatgaagctt gagaattata tccaggacaa   660
catgaagaaa gaaatggtag agatacagca gaatgcagta cagaaccaga cggctgtgat   720
gatagaaata gggacaaacc tgttgaacca aacagctgag caaacgcgga agttaactga   780
tgtggaagcc caagtattaa atcagaccac gagacttgaa cttcagctct tggaacactc   840
cctctcgaca aacaaattgg aaaaacagat tttggaccag accagtgaaa taaacaaatt   900
gcaagataag aacagtttcc tagaaaagaa ggtgctagct atggaagaca agcacatcat   960
ccaactacag tcaataaaag aagagaaaga tcagctacag gtgttagtat ccaagcaaaa  1020
ttccatcatt gaagaactag aaaaaaaaat agtgactgcc acggtgaata attcagttct  1080
tcaaaagcag caacatgatc tcatggagac agttaataac ttactgacta tgatgtccac  1140
atcaaactca gctaaggacc ccactgttgc taaagaagaa caaatcagct tcagagactg  1200
tgctgaagta ttcaaatcag gacacaccac aaatggcatc tacacgttaa cattccctaa  1260
ttctacagaa gagatcaagg cctactgtga catggaagct ggaggaggcg ggtggacaat  1320
tattcagcga cgtgaggatg gcagcgttga ttttcagagg acttggaaag aatataaagt  1380
gggatttggt aacccttcag gagaatattg gctgggaaat gagtttgttt cgcaactgac  1440
taatcagcaa cgctatgtgc ttaaaataca ccttaaagac tgggaaggga atgaggctta  1500
ctcattgtat gaacatttct atctctcaag tgaagaactc aattatagga ttcaccttaa  1560
aggacttaca gggacagccg gcaaaataag cagcatcagc caaccaggaa atgattttag  1620
cacaaaggat ggagacaacg acaaatgtat ttgcaaatgt tcacaaatgc taacaggagg  1680
ctggtggttt gatgcatgtg gtccttccaa cttgaacgga atgtactatc cacagaggca  1740
gaacacaaat aagttcaacg gcattaaatg gtactactgg aaaggctcag gctattcgct  1800
caaggccaca accatgatga tccgaccagc agatttctaa acatcccagt ccacctgagg  1860
aactgtctcg aactattttc aaagacttaa gcccagtgca ctgaaagtca cggctgcgca  1920
ctgtgtcctc ttccaccaca gagggcgtgt gctcggtgct gacgggaccc acatgctcca  1980
gattagagcc tgtaaacttt atcacttaaa cttgcatcac ttaacggacc aaagcaagac  2040
cctaaacatc cataattgtg attagacaga acacctatgc aaagatgaac ccgaggctga  2100
gaatcagact gacagtttac agacgctgct gtcacaacca agaatgttat gtgcaagttt  2160
atcagtaaat aactggaaaa cagaacactt atgttataca atacagatca tcttggaact  2220
gcattcttct gagcactgtt tatacactgt gtaaataccc atatgtcct              2269
```

METHODS AND COMPOSITIONS FOR THE TREATMENT AND DIAGNOSIS OF SYSTEMIC ANTHRAX INFECTION

CROSS REFERENCE TO RELATED APPLICATIONS

This application is a U.S. National Stage Application of International Patent Application No. PCT/US2009/001797, filed on Mar. 23, 2009, which claims priority to U.S. Provisional Application No. 61/070,581, filed on Mar. 24, 2008, each of which is herein incorporated by reference in its entirety.

BACKGROUND OF THE INVENTION

In general, the invention relates to methods and kits for the treatment and diagnosis of systemic anthrax infection.

Anthrax is an acute infectious disease caused by the spore-forming bacterium *Bacillus anthracis*. The bacterium sporulates upon contact with air and is subsequently resistant to degradation by heat, radiation, desiccation, and disinfectants. Anthrax most commonly infects wild and domestic lower vertebrates, but can infect humans (e.g., cutaneously, through inhalation, or through ingestion) when exposed to infected animals or contaminated animal products. Mortality arises from complications related to vascular injury, including increased systemic permeability, microthromboses, and shock. Hemoconcentration from the loss of water in the blood is a major manifestation of systemic anthrax, as is hemorrhagic mediastinitis.

Angiopoietins (e.g., Ang-1 and Ang-2) are secreted proteins produced by cells in the vasculature. Ang-1 is made by vascular smooth muscle. Ang-1 expression results in endothelial cell survival against injurious stimuli, the reduction of inflammatory protein expression on the surface of endothelial cells, and the maintenance of tight connections between endothelial cells to prevent vascular permeability. Conversely, Ang-2 is made by endothelial cells and antagonizes the effects of Ang-1, thus promoting inflammation. Preliminary studies have shown circulating Ang-2 rises rapidly upon systemic anthrax infection, suggesting that the level of Ang-2 in serum provides an early indicator of severe disease.

There exists a need in the art for a simple, efficient, and minimally invasive diagnostic test to identify systemic anthrax infection in a subject. In addition, effective treatments of systemic anthrax infection are needed for those diagnosed with the disease.

SUMMARY OF THE INVENTION

The present invention features methods and kits that utilize Ang-2 antagonists for the treatment and prevention of a systemic anthrax infection. The invention described herein also features methods for the diagnosis of a systemic anthrax infection by detecting elevated levels of Ang-2 in the serum of a subject.

Accordingly, the invention features a method of diagnosing a subject as having a systemic anthrax infection by measuring the level of an Ang-2 polypeptide in a sample from the subject. In a preferred embodiment, an immunological assay, such as ELISA, is used to measure the level of Ang-2 in a sample. The step of measuring Ang-2 polypeptide levels may be done on two or more occasions. In a preferred embodiment, an alteration in the levels between measurements is a diagnostic indicator of a systemic anthrax infection.

In another embodiment, the method may include comparing an Ang-2 polypeptide level in a sample to an Ang-2 polypeptide level in a normal reference. In one embodiment, an increase (e.g., 10%, 20%, 30%, 40%, 50%, 60%. 70%, 80%, 90%, 95%, 100% or more) in the level of Ang-2 polypeptide relative to the normal reference is a diagnostic indicator of systemic anthrax infection. Preferably, the normal reference is a prior sample or level taken from the subject, or a sample or level from a subject that does not have a systemic anthrax infection.

In another aspect, the invention features a method of diagnosing a subject as having a systemic anthrax infection by measuring the level of an Ang-2 nucleic acid molecule in a sample from a subject and comparing it to a reference. In one embodiment, an alteration (e.g., an increase) in the levels compared to a reference is a diagnostic indicator of a systemic anthrax infection. The step of measuring Ang-2 polypeptide levels may be done on two or more occasions. In a preferred embodiment, an alteration in the levels between measurements is a diagnostic indicator of a systemic anthrax infection.

In any of the above aspects, a level (e.g., concentration) of Ang-2 polypeptide greater than 5 ng/ml in a sample of a subject is an indicator of a systemic anthrax infection. For example, a level greater than 6 ng/ml, 10 ng/ml, 20 ng/ml, 30 ng/ml, 40 ng/ml, 50 ng/ml, 60 ng/ml, 70 ng/ml, 80 ng/ml, 90 ng/ml, or even greater than 100 ng/ml is an indicator of a systemic anthrax infection. The sample may be a bodily fluid (e.g., urine, blood, serum, plasma, or cerebrospinal fluid), cell, or tissue sample from the subject in which Ang-2 polypeptide is normally detectable. The subject is preferably a human subject.

In any of the above aspects, a subject suspected of having a system anthrax infection may be diagnosed using the methods of the invention. The methods of the invention may also be used to diagnose the severity of a systemic anthrax infection.

In another aspect, the invention features a method of treating, inhibiting, or preventing systemic anthrax infection in a subject by administering to a subject an Ang-2 antagonist in an amount sufficient to treat, inhibit, or prevent a systemic anthrax infection in the subject. Ang-2 antagonists include an antibody that specifically binds to Ang-2; an isolated Ang-1 polypeptide or biologically active fragment thereof; an Ang-1 agonist antibody; Ang-2 binding proteins that block Ang-2 binding to Tie-2 receptor; Tie-2 binding proteins that specifically block Ang-2 binding to Tie-2; soluble Tie-2 fragments that specifically bind to Ang-2; dominant active mutants of Tie-2; an antibody that binds to and activates Tie-2; agonistic Tie-2 antibodies or small molecule Tie-2 activators; antibodies that specifically bind to Tie-2 and selectively inhibit Ang-2 binding to Tie-2; upstream angiopoietin-1 regulator proteins (e.g., HIF1α or HIF2α); inhibitors of MLC phosphorylation; activators of p190RhoGAP activity; inhibitors of RhoGTPase activity; and inhibitors of Rho kinase activity.

In one embodiment, the Ang-2 antagonist is a purified antibody (e.g., a monoclonal antibody), or fragment thereof, that specifically binds to Ang-2. The monoclonal antibody may be L1-7(N) (e.g., chimeric, humanized or fully human) or an antigen-binding fragment or derivative thereof. In another embodiment, the Ang-2 antagonist is an antisense nucleobase oligomer that is at least 95% complementary to at least a portion of an Ang-2 nucleic acid sequence. The antisense nucleobase oligomer is preferably 8 to 30 nucleotides in length. In another embodiment, the Ang-2 antagonist is a small RNA having at least one strand that is at least 95% complementary to at least a portion of an Ang-2 nucleic acid sequence. The small RNA may be, e.g., a double-stranded RNA that is processed into small interfering RNAs (siRNAs) that are 19 to 25 nucleotides in length. In yet another embodiment, the method also includes administering an antibiotic or activated protein C (e.g., drotrecogin alpha). Preferably, the antibiotic is ciprofloxacin, doxycycline, erythromycin, vancomycin, or penicillin.

In another embodiment, the Ang-2 antagonist is administered to a subject within 1 hour, 2 hours, 5 hours, 10 hours, 15 hours, 20 hours, 24 hours, 30 hours, 36 hours, 40 hours, 44 hours, 48 hours, 72 hours, 96 hours, (or any number in between) or more, after a subject is infected with anthrax bacilli. The Ang-2 antagonist therapy can be continued for as long as needed, including but not limited to 1 day, 2 days, 3 days, 4 days, 5 days, 6 days, 7 days, 2 weeks, 3 weeks, 4 weeks, or more. Desirably, the Ang-2 antagonist is administered to the subject within the first 1-24 or 1-48 hours after a subject is infected with anthrax bacilli. Preferably, the Ang-2 antagonist is administered intravenously.

In another embodiment, the Ang-2 antagonist is administered to a subject identified as having or at risk of developing a systemic anthrax infection using the diagnostic methods described herein.

In yet another embodiment, the method further includes monitoring a systemic anthrax infection in a subject by measuring the level of Ang-2 polypeptide in a sample from the subject. Measuring the level of Ang-2 polypeptide may be done on two or more occasions (e.g., after initial diagnosis, exposure to anthrax, or suspicion of infection) using an immunological assay, such as ELISA. In one embodiment, a decrease in the level of Ang-2 polypeptide between measurements (e.g., over time) may be an indicator of an improvement in the systemic anthrax infection. Preferably, the level of Ang-2 polypeptide is compared to a positive reference sample and a decrease in the level of Ang-2 relative to the positive reference sample indicates an improvement in a systemic anthrax infection in a subject. The therapeutic dosage of an Ang-2 antagonist may be determined by measuring the level of Ang-2 polypeptide in a subject.

In another aspect, the invention features a kit for the diagnosis of a systemic anthrax infection in a subject. Preferably, the kit includes a nucleic acid molecule having an Ang-2 nucleic acid sequence or a sequence complementary thereto, or any combination thereof, and instructions for using the nucleic acid molecule to diagnose a systemic anthrax infection.

In yet another aspect, the invention features a kit that includes an Ang-2 binding molecule and instructions for the use of an Ang-2 binding molecule for the diagnosis of a systemic anthrax infection. Preferably, the Ang-2 binding molecule is an antibody, or antigen-binding fragment thereof, that specifically binds Ang-2.

For any of the kits described above, the kit can further include a reference sample or level or standard curve that is either a normal Ang-2 reference or a positive Ang-2 reference. In some examples a single kit can include both references.

In another aspect, the invention features a kit that include sand Ang-2 antagonist and instructions for the use of the Ang-2 antagonist for the treatment or prevention of a systemic anthrax infection.

By "alteration" is meant a change (e.g., an increase or decrease). The alteration can be in the expression levels of an Ang-2 nucleic acid or polypeptide as detected by methods known to one of skill in the art, such as those described below. As used herein, an alteration includes a 10% change in expression levels, preferably a 25% change, more preferably a 40%, 50%, 60%, 70%, 80%, 90%, 95%, 96%, 97%, 98%, 99%, or greater change in expression levels. "Alteration" can also include a change (e.g., an increase or decrease) in the biological activity of an Ang-2 nucleic acid or polypeptide. As used herein, an alteration includes a 10% change in biological activity, preferably a 25% change, more preferably a 40%, 50%, 60%, 70%, 80%, 90%, 95%, 96%, 97%, 98%, 99%, or greater change in biological activity. Examples of biological activity for Ang-2 polypeptides are described below.

By "angiopoietin-1" or "Ang-1" is meant a polypeptide, or a nucleic acid sequence that encodes it, that is substantially identical or homologous to any of the following amino acid sequences: the amino acid sequence of FIG. 11, the nucleic acid sequence of FIG. 12, GenBank Accession Numbers NM_001146, NP_001137, and BAB91325, or fragments thereof, and/or that has Ang-1 biological activity, as described below. Ang-1 is a secreted protein that is approximately 55 kDa in size and the glycosylated forms can be approximately 70 kDa. Ang-1 nucleic acid molecules encode an Ang-1 polypeptide and preferably have substantial identity to the nucleic acid sequence set forth in FIG. 12. Ang-1 can also include fragments, derivatives, or analogs of Ang-1 that preferably retain at least 25%, 30%, 40%, 50%, 60%, 70%, 80%, 90%, 95%, 96%, 97%, 98%, 99%, or more of Ang-1 biological activity (e.g., binding to the Tie-2 receptor). Ang-1 polypeptides may be isolated from a variety of sources (e.g., from mammalian tissue, mammalian cells, or from another source) or prepared by recombinant or synthetic methods.

The term "Ang-1" also encompasses modifications to the polypeptide, fragments, derivatives, analogs, and variants of the Ang-1 polypeptide. Preferred Ang-1 fragments or variants useful in the methods of the invention include fragments or variants that can antagonize the function of Ang-2, for example, by binding to the Tie-2 receptor and blocking Ang-2 binding to the Tie-2 receptor. Alternatively, Ang-1 fragments, derivatives, analogs, and variants can activate Rac1 or p190RhoGAP, which can inhibit or suppress RhoA kinase activity. Ang-1 is also known as "ANGPT1," "AGPT," "AGP1," and "angiopoietin-1 precursor," all of which are encompassed by the term "Ang-1."

By "Ang-1 biological activity" is meant one or more of the following activities: binding to the Tie-2 receptor, activation of the Tie-2 receptor, induction of Tie-2 phosphorylation, pro-angiogenic or anti-angiogenic activity depending on the environment (Stoeltzing et al., *Cancer Res.* 63: 3370-3377, 2003), activation of p190RhoGAP, activation of Rac1, down-regulation or inhibition of RhoA kinase activity, inhibition of vascular permeability, promotion of tumor angiogenesis and tumor vessel plasticity, promotion of endothelial cell survival, anti-inflammatory activity, reduction in expression of inflammatory molecules (e.g., ICAM-1), and blood vessel development. Assays for Ang-1 biological activity are known in the art and include, e.g., Tie-2 receptor binding assays, Tie-2 receptor activation assays, Tie-2 phosphorylation assays, in vitro and in vivo angiogenesis assays, and vascular permeability assays.

By "angiopoietin-2" or "Ang-2" is meant a polypeptide, or a nucleic acid sequence that encodes it, that is substantially identical or homologous to any of the following amino acid sequences: the amino acid sequence of FIG. 13, the nucleic acid sequence of FIG. 14, GenBank Accession Numbers NM_001147, NP_001138, and BAA95590 or fragments thereof, and/or that has Ang-2 biological activity, as described below. Ang-2 is a secreted protein that is approximately 55 kDa in size and the glycosylated forms can be approximately 70 kDa (see, for example, Maisonpierre et al., *Science* 277: 55, 1997). Ang-2 nucleic acid molecules encode an Ang-2 polypeptide and preferably have substantial identity to the nucleic acid sequence described by the sequence of FIG. 14. Ang-2 can also include fragments, derivatives, or analogs of Ang-2 that preferably retain at least 25%, 30%, 40%, 50%, 60%, 70%, 80%, 90%, 95%, 96%, 97%, 98%, 99%, or more of Ang-2 biological activity. Ang-2 polypeptides may be isolated from a variety of sources (e.g., mammalian tissue, mammalian cells, or from another source) or may be prepared by recombinant or synthetic methods. The term "Ang-2" also encompasses modifications made to the polypeptide, or fragments, derivatives, analogs, and variants of the Ang-2 polypeptide. Ang-2 is also known as "ANGPT2" and "angiopoietin-2 precursor," both of which are encompassed by the term "Ang-2."

By "Ang-2 biological activity" is meant one or more of the following activities: antagonism of Ang-1 activity, binding to the Tie-2 receptor, inhibition of phosphorylation of the Tie-2 receptor, inhibition of Tie-2 receptor signaling, disruption of blood vessel formation, destabilization of blood vessels, induction of vascular permeability, induction in the expression of inflammatory molecules (e.g., ICAM-1), and modulation of angiogenesis. Assays for Ang-2 activity are known in the art and include, e.g., Tie-2 receptor binding assays, Tie-2 receptor activation assays, Tie-2 phosphorylation assays, in vitro and in vivo angiogenesis assays, and vascular permeability assays.

By "Ang-2 antagonist" is meant any compound (e.g., small molecule compound, polypeptide (e.g., synthetic or natural), nucleic acid molecule, antibody; or fragments and functional derivatives thereof) that inhibits, reduces, or prevents Ang-2 expression or Ang-2 biological activity by, e.g., reducing or inhibiting Ang-2 protein synthesis, reducing Ang-2 nucleic acid levels, preventing or inhibiting Ang-2 binding to the Tie-2 receptor, or reducing or inhibiting the Ang-2 signaling pathway downstream of the Tie-2 receptor. Non-limiting examples of Ang-2 antagonists include, e.g., antibodies (e.g., neutralizing antibodies) or fragments thereof, that specifically bind to Ang-2; Ang-1 or biologically active peptide fragments thereof; Ang-1 agonist antibodies; nucleic acid molecules that decrease Ang-2 expression (e.g., small RNA or antisense nucleic acid molecules); antibodies that bind to and activate the Tie-2 receptor; agonistic antibodies or small molecule compounds that activate the Tie-2 receptor; Ang-2 binding proteins that prevent binding of Ang-2 to the Tie-2 receptor; antibodies that specifically bind to the Tie-2 receptor and prevent Ang-2 binding to Tie-2, but not Ang-1 binding to Tie-2; soluble Tie-2 fragments that bind to Ang-2; dominant negative Tie-2 mutants that are constitutively active (Vikkula et al., *Cell* 87: 1181-1190, 1996); and upstream angiopoietin-1 regulator proteins (e.g., HIF1α of HIF2α). Examples of Ang-2 antagonist antibodies that specifically bind the Ang-2 polypeptide include, e.g., L1-7(N) (Oliner et al., *Cancer Cell* 6: 507-516, 2004), anti-Ang-2 antibodies from Research Diagnostics Inc. (e.g., Catalog Nos. RDI-ANGIOP2XabR, RDI-ANG218NabG, and RDI-MANGIOP2abrx), and anti-Ang-2 antibodies from AbCam Inc. (e.g., Catalog Nos. Ab18518, Ab8452, and Ab10601). Non-limiting examples of Ang-2 antagonists that function downstream of the Tie-2 receptor include, e.g., activators of p190RhoGAP or Rac1 activity or expression levels, inhibitors of MLC phosphorylation, inhibitors of RhoA GTPase activity or expression levels, inhibitors of Rho kinase activity or expression levels, and inducers of Tie-2 phosphorylation. Desirably, the Ang-2 antagonist will inhibit, reduce, or prevent Ang-2 expression or biological activity by at least 10%, preferably 20%, 30%, 40%, 50%, 60%, 70%, 80%, 90%, 95%, or more. Ang-2 antagonists can be assayed for efficacy using any of the structural, functional, and molecular assays described herein or known in the art. Examples of such assays include, e.g., functional assays (e.g., phenotypic observations of spindle phenotype, thick actin stress fibers, or paracellular gap formation; determination of an increase in vascular barrier integrity; or determination of the elimination of a systemic anthrax infection), structural assays (e.g., FITC-albumin permeability assays or transendothelial resistance (TER) measurements), and molecular assays (e.g., inhibition of MLC phosphorylation, inhibition of Rho kinase activity, induction of Tie-2 phosphorylation, activation of PI-3 kinase activity, activation of Rac1, activation of p190RhoGAP, and activation of protein kinase C activity). In one example, the Ang-2 antagonist or a functional derivative thereof will increase vascular barrier integrity (e.g., as assessed by TER measurements) by at least about 10%, 20%, 30%, 40%, 50%, 60%, 70%, 80%, 90%, or 100% in a TER assay relative to a control (i.e., the same assay where the cells have not been exposed to an Ang-2 antagonist or functional derivative thereof).

By "antisense nucleobase oligomer" is meant a nucleobase oligomer, regardless of length, that is complementary to all or a portion of the coding strand or mRNA of an Ang-2 gene or nucleic acid sequence. By a "nucleobase oligomer" is meant a compound that includes a chain of at least eight nucleobases, preferably at least twelve, and most preferably at least sixteen bases, joined together by linkage groups. Included in this definition are, e.g., natural and non-natural oligonucleotides, both modified and unmodified, as well as oligonucleotide mimetics such as protein nucleic acids, locked nucleic acids, and arabinonucleic acids. Numerous nucleobases and linkage groups may be employed in the nucleobase oligomers of the invention, including those described in U.S. Patent Publication Nos. 2003/0114412 (see, for example, paragraphs 27-45 of the publication) and 2003/0114407 (see, for example, paragraphs 35-52 of the publication), incorporated herein by reference. The nucleobase oligomer can also be targeted to the translational start and stop sites. Preferably, the antisense nucleobase oligomer comprises from about 8 to 30 nucleotides. The antisense nucleobase oligomer can also contain at least 40, 60, 85, 120, or more consecutive nucleotides that are complementary to all or a portion of Ang-2 mRNA or DNA and may be as long as the full-length mRNA or gene.

By "expression" is meant the detection of a gene or polypeptide by methods known to one of skill in the art. For example, polypeptide expression is often detected by Western blotting, DNA expression is often detected by Southern blotting or polymerase chain reaction (PCR), and RNA expression is often detected by Northern blotting, PCR, or RNAse protection assays.

By "fragment" is meant a portion of a polypeptide or nucleic acid molecule that contains at least, e.g., 10%, 20%, 30%, 40%, 50%, 60%, 70%, 80%, 90%, 95%, or more of the entire length of the reference nucleic acid molecule or polypeptide. A fragment may contain, e.g., 10, 20, 30, 40, 50, 60, 70, 80, 90, or 100, 200, 300, 400, 500, 600, 700, 800, 900, 1000, 1100, 1200, 1300, 1400, 1500, 2000, 2500, 3000, 4000, or 4500 nucleotides or more nucleotides, up to the full length of the nucleic acid, or 10, 20, 30, 40, 50, 60, 70, 80, 90, 100, 150, 200, 250, 300, 350, 400, 450, or 500 amino acids or more amino acids, up to the full length of the protein. Preferred fragments useful in the therapeutic methods of the invention include, e.g., Ang-1 peptide fragments that retain Ang-1 biological activity and soluble Tie-2 fragments that can bind to Ang-2. Fragments can be modified as described herein and as known in the art.

By "heterologous" is meant any two or more nucleic acid or polypeptide sequences that are not normally related to each other in nature. For instance, a heterologous nucleic acid is typically recombinantly produced, having two or more sequences, e.g., from unrelated genes, arranged to make a new functional nucleic acid (e.g., a promoter from one source and a coding region from another source). Similarly, a heterologous polypeptide will often refer to two or more subsequences that are not found in the same relationship to each other in nature (e.g., a fusion protein).

By "homologous" is meant any gene or polypeptide sequence that bears at least 30% homology, more preferably 40%, 50%, 60%, 70%, 80%, and most preferably 90%, 95%, 96%, 97%, 98%, 99%, or more homology to a known gene or polypeptide sequence over the length of the comparison sequence. A "homologous" polypeptide can also have at least one biological activity of the comparison polypeptide. For polypeptides, the length of comparison sequences will generally be at least 16 amino acids, preferably at least 20 amino acids, more preferably at least 30, 40, 50, 60, 70, 80, 90, 100, 150, 200, 250, 300, 350, 400, 450, or 500 amino acids or more. For nucleic acids, the length of comparison sequences will generally be at least 50 nucleotides, preferably at least 60, 70, 80, 90, 100, 150, 200, 250, 300, 350, 400, 450, 500, 550, 600, 700, 800, 900, 100, 1100, 1200, 1300, 1400, 1500, or more. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein or polypeptide.

"Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic or antagonistic properties described herein. The monoclonal antibodies herein include chimeric, hybrid and recombinant antibodies produced by splicing a variable (including hypervariable) domain of the antibody of interest with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

The term "monoclonal antibody," as used herein, refers to an antibody obtained from a population of substantially homogeneous antibodies (i.e., the individual antibodies comprising the population are identical except for possible naturally occurring mutations that may be present in minor amounts). Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256: 495, 1975, or may be made by recombinant DNA methods (see, e.g., U.S. Pat. No. 4,816,567). The "monoclonal antibodies" may also be isolated from phage antibody libraries using the techniques described in Clackson et al., *Nature* 352: 624-628, 1991 and Marks et al., *J. Mol. Biol.* 222: 581-597, 1991, for example.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (e.g., the "import" sequences).

Generally, a humanized antibody has one or more amino acid residues introduced into it from a source that is non-human. In general, the humanized antibody will comprise substantially all of at least one, and typically two, variable domains (Fab, Fab', F(ab')$_2$, Fabc, or Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region" is meant the sequences of amino acids located on either side of the three hypervariable sequences of the immunoglobulin light and heavy chains.

The FR and CDR regions of the humanized antibody need not correspond precisely to the parental sequences (e.g., the import CDR or the consensus FR may be mutagenized by substitution, insertion, or deletion of at least one residue so that the CDR or FR residue at that site does not correspond to either the consensus or the import antibody). Such mutations, however, will not be extensive. Usually, at least 75%, preferably 90%, and most preferably at least 95% of the humanized antibody residues will correspond to those of the parental FR and CDR sequences.

By "p190RhoGAP" is meant a multi-domain 190 kDa protein that localizes to the cytoplasm of cultured cells and appears to function as an inhibitor of cell proliferation and as an inducer of apoptosis. p190RhoGAP contains a RhoGAP domain that activates the intrinsic GTPase activity of the Rho family of small GTPases, which regulate actin cytoskeleton rearrangements in response to growth factor or integrin stimulation. p190RhoGAP is also tyrosine phosphorylated and a substrate of c-Src.

By "pharmaceutically acceptable carrier" is meant a carrier that is physiologically acceptable to the treated subject while retaining the therapeutic properties of the compound (e.g., Ang-2 antagonist) with which it is administered. One exemplary pharmaceutically acceptable carrier substance is physiological saline. Other physiologically acceptable carriers and their formulations are known to one skilled in the art and are described, for example, in Remington's Pharmaceutical Sciences, (20$^{th}$ edition), ed. A. Gennaro, 2000, Lippincott, Williams & Wilkins, Philadelphia, Pa.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter or an array of transcription factor binding sites) and a second nucleic acid sequence, wherein the expression control sequence directs transcription of the nucleic acid corresponding to the second sequence.

By "protein," "polypeptide," or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide. A polypeptide (or fragment thereof) may be said to be "isolated" or "substantially pure" when physical, mechanical, or chemical methods have been employed to remove the polypeptide from cellular constituents. An "isolated polypeptide," "substantially pure polypeptide," or "substantially pure and isolated polypeptide" is typically considered removed from cellular constituents and substantially pure when it is at least 60% by weight free from the proteins and naturally occurring organic molecules with which it is naturally associated. Preferably, the polypeptide is at least 75%, more preferably at least 90%, and most preferably at least 99% by weight pure. A substantially pure polypeptide may be obtained by standard techniques, for example, by extraction from a natural source (e.g., lung tissue or cell lines), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis. Alternatively, a polypeptide is considered isolated if it has been altered by human intervention, placed in a location that is not its natural site, or if it is introduced into one or more cells.

By "purified" or "isolated" is meant at least 60% by weight free from proteins and other molecules (e.g., naturally occurring or synthetic) with which it is naturally associated. Preferably, the preparation is at least 75%, more preferably 90%, and most preferably at least 99% by weight purified or isolated.

By "reduce or inhibit" is meant the ability to cause an overall decrease preferably of 20% or greater, more preferably of 50% or greater, and most preferably of 75%, 80%, 85%, 90%, 95%, or greater. For therapeutic applications, to "reduce or inhibit" can refer to the symptoms of the disorder being treated or the presence or extent of a systemic anthrax infection being treated. Symptoms of a systemic anthrax infection include, e.g., increased systemic permeability, microthromboses, hemoconcentration, hemorrhaging (e.g., hemorrhagic mediastinitis), shock (e.g., septic shock), respiratory distress (e.g., chest pain, difficulty breathing, dyspnea, stridor, cyanosis, or non-productive coughing), nausea, vomiting, diarrhea (e.g., bloody diarrhea), ascites, systemic inflammation (e.g., indicated by fever, leukocytosis, tachypnea, and/or tachycardia), inflammation of the intestinal tract, loss of appetite, skin lesions (e.g., eschars), sore throat, lymphadenopathy, fever, muscle ache, malaise, fatigue, myalgias, profound sweating, abdominal pain, or hematemesis. For diagnostic or monitoring applications, to "reduce or inhibit" can refer to a decrease in the level of protein or nucleic acid detected by the aforementioned assays.

By "reference" is meant any sample, standard, or level that is used for comparison purposes. A "normal reference sample" can be a prior sample taken from the same subject prior to the onset of a systemic anthrax infection; a sample from a subject not having a systemic anthrax infection; a subject that has been successfully treated for systemic anthrax infection; or a sample of a purified reference Ang-2 polypeptide at a known normal concentration. By "reference standard or level" is meant a value or number derived from a reference sample. A normal reference standard or level can be a value or number derived from a normal subject that is matched to the sample subject by at least one of the following criteria: age, weight, disease stage, and overall health. In one example, a normal reference level of Ang-2 is less than 5 ng/ml in a serum sample, preferably less than 4 ng/ml, 3 ng/ml, 2 ng/ml, or 1 ng/ml of Ang-2 in a serum sample. A "positive reference" sample, standard, or value is a sample, standard, value, or number derived from a subject that is known to have a systemic anthrax infection that is matched to the sample subject by at least one of the following criteria: age, weight, disease stage, and overall health. For example, a positive reference value for Ang-2 is greater than 5 ng/ml serum, preferably greater than greater than 6 ng/ml, 10 ng/ml, 20 ng/ml, 30 ng/ml, 40 ng/ml, 50 ng/ml, 60 ng/ml, 70 ng/ml, 80 ng/ml, 90 ng/ml, or even greater than 100 ng/ml serum.

By "Rho" is meant a member of the Rho family of GTPases. The Rho family of GTPases is a family of proteins that couples extracellular signaling events to changes in cellular function, including endocytosis. The Rho family includes at least fifteen members and their isoforms, including, e.g., the Rho subfamily (A, B, and C isoforms), the Rac subfamily (1, 2, and 3 isoforms), Cdc42 (the Cdc42Hs and G25K splice variants), Chp, the Rnd subfamily (Rnd1, Rnd2, and Rnd3 isoforms), RhoD, RhoG, RhoH, and TC10 (see, e.g., Wherlock et al., *J. Cell Sci.* 115: 239-240, 2002). For each subfamily, it will be understood that while the specification refers specifically to one family member (e.g., RhoA or Rac1), additional members of the subfamily may be used in the invention as well. Rho family members, like all GTPases, cycle between an inactive GDP-bound state and an active GTP-bound state. The activity of Rho GTPases is modulated by several accessory proteins, including, e.g., guanine nucleotide exchange factors (GEFs), GTPase-activating proteins (GAPs), and GDP dissociation inhibitors (GDIs). GEFs, as their name implies, stimulate Rho family members to exchange GDP for GTP, resulting in GTPase activation. GAPs (e.g., p190RhoGAP) stimulate the Rho GTPase to hydrolyze its bound GTP, returning the Rho protein to its inactive GDP-bound state. GDIs preferentially bind Rho-GDP and modulate the activation and targeting of Rho-GDP to the membrane. Upon activation, Rho GTPases interact with a plethora of downstream effector molecules that, in turn, modulate cellular function.

By "Rho kinase" is meant a serine-threonine kinase that serves as a substrate for Rho family members and mediates cellular functions, including, e.g., focal adhesions, motility, smooth muscle contraction, and cytokinesis. Rho kinase also modulates the phosphorylation of the myosin light chain (MLC) of myosin.

By "small RNA" is meant any RNA molecule, either single-stranded or double-stranded," that is at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Preferably, the small RNA is capable of mediating RNAi. As used herein, the phrase "mediates RNAi" refers to the ability to distinguish which RNAs are to be degraded by the RNAi machinery or process. Included within the term "small RNA" are "small interfering RNAs" and "microRNA." In general, microRNAs (miRNAs) are small (e.g., 17-26 nucleotides), single-stranded non-coding RNAs that are processed from approximately 70 nucleotide hairpin precursor RNAs by the protein dicer. Small interfering RNAs (siRNAs) are a similar size and are also non-coding. However, siRNAs are processed from long double-stranded RNAs and, thus, are usually double stranded. siRNAs can also include, e.g., short hairpin RNAs in which both strands of an siRNA duplex are included within a single RNA molecule. Small RNAs can be used to describe both types of RNA. These terms include double-stranded RNA, single-stranded RNA, isolated RNA (e.g., partially purified RNA, essentially pure RNA, synthetic RNA, or recombinantly produced RNA), as well as altered RNA that differs from naturally occurring RNA by the addition, deletion, substitution, and/or alteration of one or more nucleotides. Such alterations can include, e.g., addition of non-nucleotide material to the end(s) of the small RNA or internally (at one or more nucleotides of the RNA). Nucleotides in the RNA molecules of the present invention can also include non-standard nucleotides, including non-naturally occurring nucleotides or deoxyribonucleotides. In a preferred embodiment, the RNA molecules contain a 3' hydroxyl group.

By "specifically binds" is meant a compound or antibody which recognizes and binds a polypeptide of the invention, but that does not substantially recognize and bind other molecules in a sample (e.g., a biological sample) which naturally includes a polypeptide of the invention. In one example, an antibody that specifically binds Ang-2 does not specifically bind Ang-1.

By "subject" is meant a mammal, including, but not limited to, a human or non-human mammal, such as a bovine, equine, canine, ovine, or feline.

By "substantially identical" is meant a nucleic acid or amino acid sequence that, when optimally aligned (e.g., using the methods described below) share at least 60%, 65%, 70%, 75%, 80%, 85%, 90%, 95%, 96%, 97%, 98%, 99%, or 100% sequence identity with a second nucleic acid or amino acid sequence (e.g., an Ang-2 sequence). "Substantial identity" may be used to refer to various types and lengths of sequence, such as, e.g., full-length sequences, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith and Waterman, *J Mol Biol* 147:195-7, 1981); "BestFit" (Smith and Waterman, in "Advances in Applied Mathematics," pp. 482-489, 1981) as incorporated into GeneMatcher Plus™, Schwarz and Dayhof, "Atlas of Protein Sequence and Structure," Dayhof, M. O., Ed, pp 353-358, 1979; BLAST program (Basic Local Alignment Search Tool; Altschul et al., *J. Mol. Biol.* 215:403-10, 1990), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be, e.g., at least 10 amino acids, preferably 20, 30, 40, 50, 60, 70, 80, 90, 100, 110, 120, 130, 140, 150, 200, 250, 300, 350, 400, 450, or 500 amino acids or more. For nucleic acids, the length of comparison sequences will generally be at least 25, 50, 100, 125, 150, 200, 250, 300, 350, 400, 450, 500, 550, or at least 600, 700, 800, 900, 1000, 1100, 1200, 1300, 1400, or 1500 nucleotides or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "systemic anthrax infection" is meant an infection caused by *Bacillus anthracis* bacteria or spores of the *Bacillus anthracis* bacteria, wherein the bacteria has spread actively or passively throughout the anatomy of a subject and is disseminated throughout different systems of the subject (e.g., digestive, respiratory, or circulatory system). The bacteria can enter the subject through, for example, the intestines (e.g., ingestion), lungs (e.g., inhalation), or skin (e.g., cutaneous).

By "therapeutic amount" is meant an amount that, when administered to a subject suffering from a systemic anthrax infection, is sufficient to cause a qualitative or quantitative reduction in the symptoms associated with the infection, for example, as described below.

By "treating" is meant administering a compound (e.g., an Ang-2 antagonist) or a pharmaceutical composition for therapeutic purposes, or administering treatment to a subject already suffering from a disease to improve the subject's condition. By "treating a systemic anthrax infection" is meant that the infection and the symptoms associated with the infection are, e.g., alleviated, reduced, cured, or placed in a state of remission. More specifically, when Ang-2 antagonist compounds, or fragments or derivatives thereof, are used to treat a subject with a systemic anthrax infection, it is generally provided in a therapeutically effective amount to achieve any one or more of the following: reduce mortality, reduce organ or tissue damage, reduce internal bleeding, prevent shock (e.g., septic shock), decrease time to resolution of shock, decrease skin lesions (e.g., eschars), decrease gastrointestinal distress, decrease respiratory distress, decrease systemic permeability, decrease microthromboses, decrease hemoconcentration, decrease hemorrhaging (e.g., hemorrhagic mediastinitis), and decrease hospitalization time.

By "vector" is meant a DNA molecule, usually derived from a plasmid or bacteriophage, into which fragments of DNA may be inserted or cloned. A recombinant vector will contain one or more unique restriction sites and may be capable of autonomous replication in a defined host or vehicle organism such that the cloned sequence is reproducible. A vector contains a promoter that is operably linked to a gene or coding region such that, upon transfection into a recipient cell, an RNA is expressed.

Other features and advantages of the invention will be apparent from the following Detailed Description, the drawings, and the claims.

BRIEF DESCRIPTION OF THE DRAWINGS

FIG. 1 shows elevation of Ang-2 levels over time in baboons infected with $6\times10^9$ CFU/kg of anthrax bacilli.

FIG. 2 shows elevation of Ang-2 levels over time in baboons infected with $1\times10^9$ CFU/kg of anthrax bacilli.

FIG. 3 shows elevation of Ang-2 levels over time in baboons infected with $5\times10^6$ CFU/kg of anthrax bacilli.

FIG. 4 shows elevation of Ang-2 levels over time in baboons infected with $5\times10^5$ CFU/kg of anthrax bacilli.

FIG. 5 shows elevation of Ang-2 levels over a ten-hour time period in baboons infected with $6 \times 10^9$ and $1 \times 10^9$ CFU/kg of anthrax bacilli.

FIG. 8 shows the effects of pre-treating baboons with activated protein C prior to infection with the anthrax bacilli. Lines with filled squares represent animals treated with $6 \times 10^9$ bacilli only. Lines with open squares represent animals pre-treated with activated protein C prior to infection with $6 \times 10^9$ bacilli. Lines with diamonds represent animals treated with $5 \times 10^6$ bacilli only.

Figure 9:
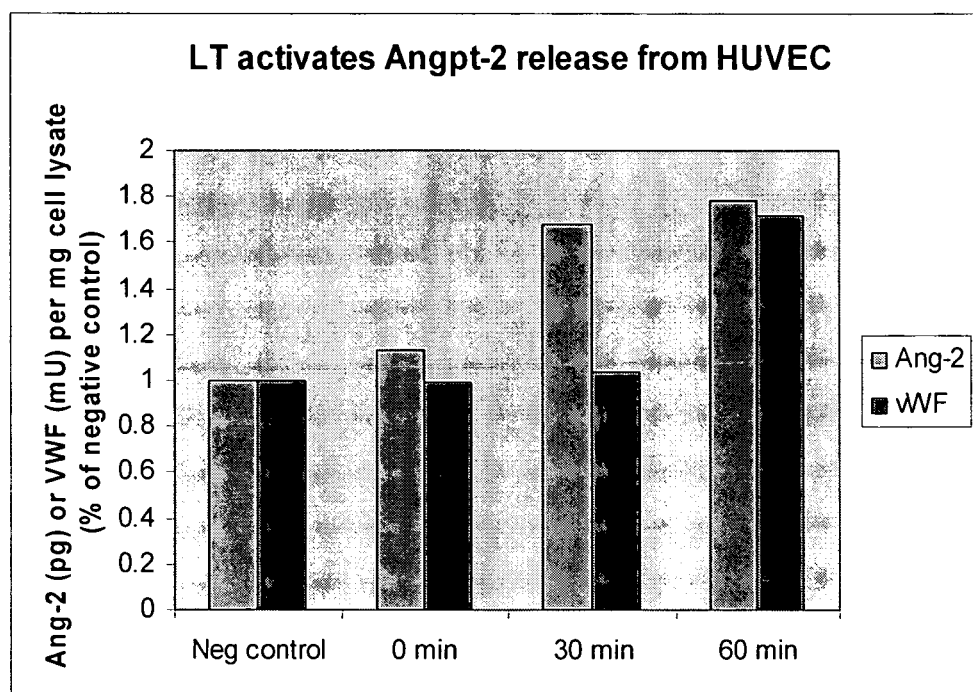

FIG. 9 shows HUVECs treated with 1 mg/ml lethal toxin (LT), a component of the anthrax toxin. Accumulation of Ang-2 was measured in the conditioned media by commercial ELISA. Ang-2 measurements were normalized against protein content of the cell lysate. To enable comparison with von Willebrand factor (vWF, measured by commercial ELISA), values are presented as a percentage of the negative control. Levels of both Ang-2 and vWF rose shortly after LT treatment.

Figure 10:
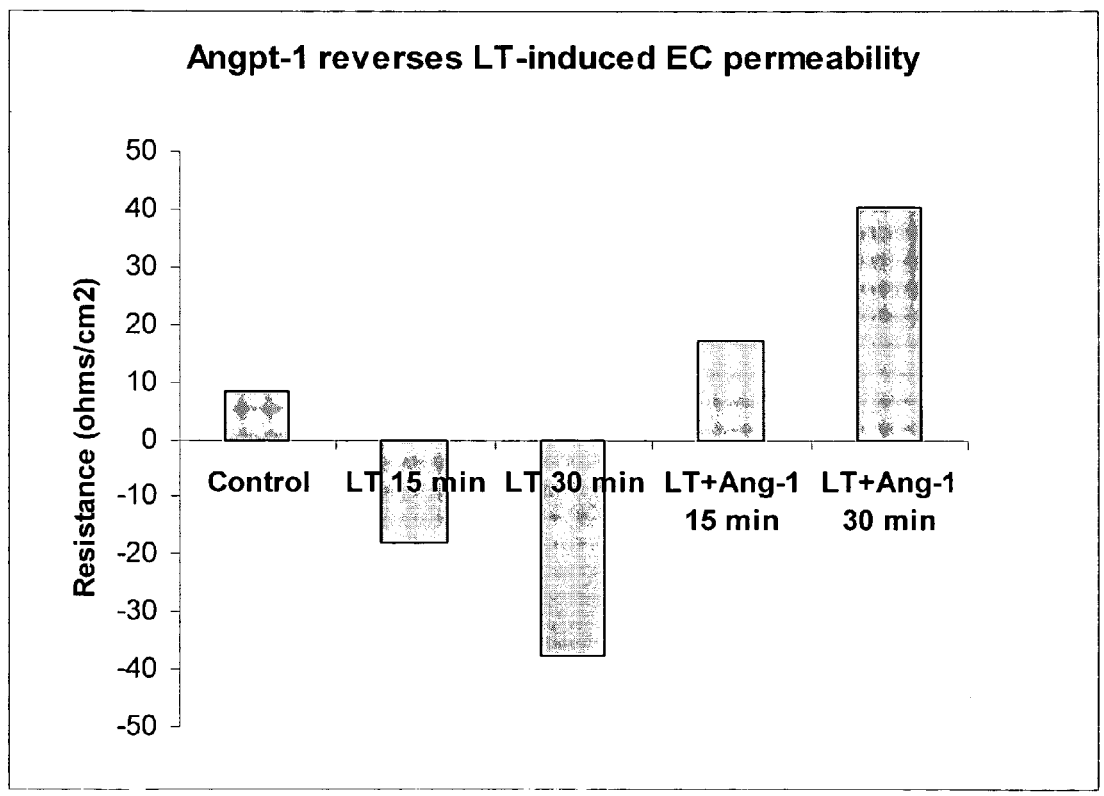

FIG. 10 shows a progressive increase in cell permeability observed in HUVECs treated with LT. Co-incubation of HUVECs with Ang-1 fortifies the barrier function of the endothelial cells.

Figure 11:
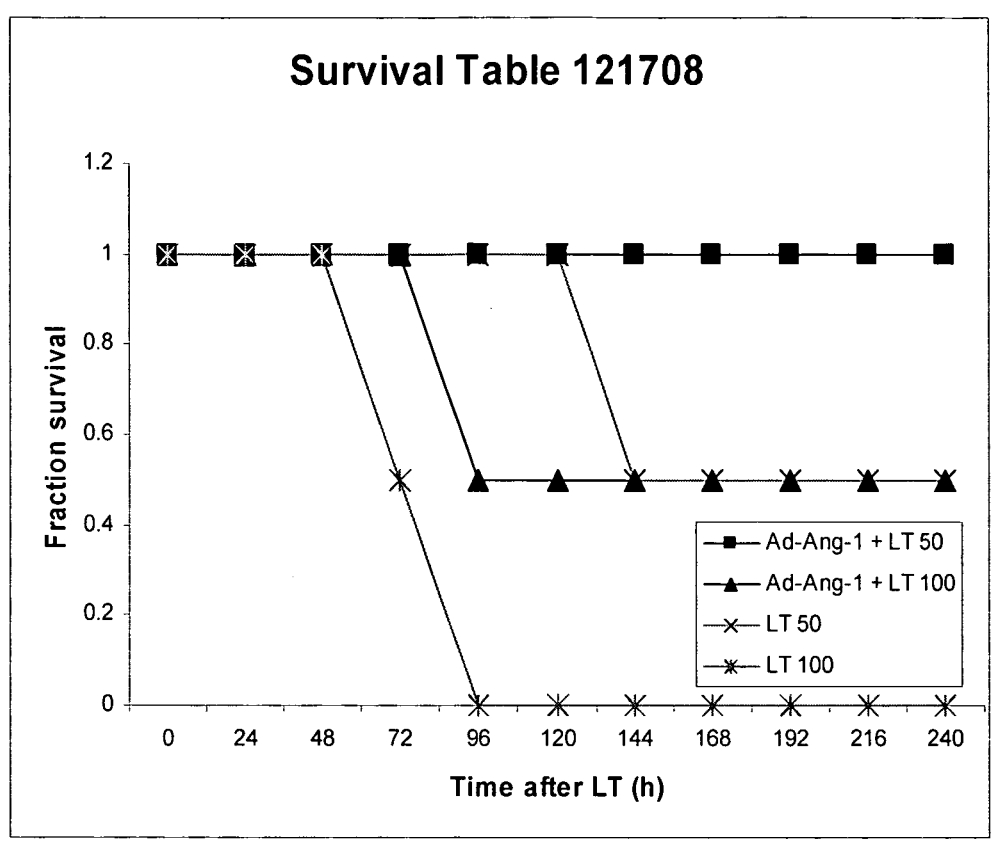

FIG. 11 shows a survival plot of mice upon anthrax challenge following treatment with adenovirus encoding human Ang-1 or with saline control. 8-week-old C57BL6/J male mice were administered 50 or 100 µg of anthrax LT (LT 50, LT 100 respectively) by tail vein, 48 hours prior to which they were either treated with 0.9% saline intravenously or $10^9$ particles of recombinant adenovirus encoding human Ang-1 suspended in 0.9% saline (Ad-Ang-1, a recombinant adenovirus that is commonly used to induce transient systemic overexpression of the inserted gene).

FIG. 12 shows the amino acid sequence of Ang-1 (SEQ ID NO:1).

FIG. 13 shows the nucleic acid sequence of Ang-1 (SEQ ID NO:2).

FIG. 14 shows the amino acid sequence of Ang-2 (SEQ ID NO:3).

FIG. 15 shows the nucleic acid sequence of Ang-2 (SEQ ID NO:4).

DETAILED DESCRIPTION

Anthrax is a bacterial infection caused by the bacterium *Bacillus anthracis*. The bacteria produce an anthrax toxin that is often lethal. We have found that systemic anthrax infection results in an increase in the level of circulating Ang-2 in an infected subject. We have also found that the rise in Ang-2 levels in serum (e.g., blood) of an infected subject occurs early in infection and persists for the first 24-48 hours (e.g., post-infection) and subsides in those subjects that survive the bacterial challenge. In addition, we have demonstrated that the magnitude of the increase of circulating Ang-2 correlates with the initial dose of the anthrax bacilli that infects the subject. Increased Ang-2 levels may be pathogenic, resulting in inflammation, vascular leak, and thrombosis associated with systemic anthrax infections. In sum, these results suggest a causal role for Ang-2 in systemic anthrax infections and suggest that Ang-2 may serve as a diagnostic in the identification of such infections.

Accordingly, the invention features the use of therapeutic compounds that function as Ang-2 antagonists. Ang-2 antagonists include any synthetic or natural polypeptide or small molecule compound that can decrease the levels of Ang-2 or reduce or block Ang-2 signaling, either by affecting Ang-2 directly or by affecting upstream or downstream effector molecules or regulators of Ang-2 signaling pathways. Non-limiting examples of therapeutic compounds useful in the methods of the invention are described in detail below. In addition, the invention features the measurement of Ang-2 levels for the diagnosis of a systemic anthrax infection.

Nucleic Acid-Based Therapeutics

The present invention features therapeutic nucleic acids that can be used to decrease the levels of Ang-2 for the treatment of systemic anthrax infections. Such therapeutic nucleic acids include, e.g., antisense nucleobase oligomers or small RNAs to downregulate expression of Ang-2 mRNA directly.

By binding to the complementary nucleic acid sequence (e.g., the sense or coding strand), antisense nucleobase oligomers are able to inhibit protein expression, presumably through the enzymatic cleavage of the RNA strand by RNAse H. Preferably, the antisense nucleobase oligomer is capable of reducing Ang-2 protein expression in a cell that expresses increased levels of Ang-2. Preferably, the decrease in Ang-2 protein expression is at least 10% relative to cells treated with a control nucleobase oligomer, preferably 20% or greater, more preferably 40%, 50%, 60%, 70%, 80%, 90%, or greater. Methods for selecting and preparing Ang-2 antisense nucleobase oligomers are well known in the art. For an example of the use of antisense nucleobase oligomers for the downregulation of VEGF expression, see, e.g., U.S. Pat. No. 6,410,322, incorporated herein by reference. Methods for assaying levels of protein expression are also well known in the art and include, e.g., Western blotting, immunoprecipitation, and ELISA.

One example of an antisense nucleobase oligomer particularly useful in the methods and compositions of the invention is a morpholino oligomer. Morpholinos are used to block access of other molecules to specific sequences within nucleic acid molecules. They can block access of other molecules to small (~25 base) regions of ribonucleic acid (RNA). Morpholinos are sometimes referred to as phosphorodiamidate morpholino oligos or PMOs.

Morpholinos are used to knock down gene function by preventing cells from making a targeted protein or by modifying the splicing of pre-mRNA. Morpholinos are synthetic molecules that bind to complementary sequences of RNA by standard nucleic acid base-pairing. While morpholinos have standard nucleic acid bases, those bases are bound to morpholine rings instead of deoxyribose rings and are linked through phosphorodiamidate groups instead of phosphates. Replacement of anionic phosphates with the uncharged phosphorodiamidate groups eliminates ionization in the usual physiological pH range, so morpholinos in organisms or cells are uncharged molecules.

Morpholinos act by "steric blocking" or binding to a target sequence within an RNA and blocking molecules which might otherwise interact with the RNA. Because of their completely unnatural backbones, morpholinos are not recognized by cellular proteins. Nucleases do not degrade morpholinos and morpholinos do not activate toll-like receptors. As such, morpholinos do not activate innate immune responses such as, e.g., the interferon system or the NF-κB mediated inflammation response. Morpholinos are also not known to modify the methylation state of nucleic acids. Therefore, morpholinos directed to any part of Ang-2 and that reduce or inhibit the expression levels or biological activity of Ang-2 by, e.g., at least 10%, 20%, 30%, 40%, 50%, 60%, 70%, 80%, 90%, or more, are particularly useful in the methods and compositions of the invention.

The present invention also features the use of RNA interference (RNAi) to inhibit expression of Ang-2. RNAi is a form of post-transcriptional gene silencing initiated by double-stranded RNA (dsRNA). Short (e.g., 15 to 35 nucleotides in length) double-stranded RNAs, known generally as "siRNAs," "small RNAs," or "microRNAs," are effective at down-regulating gene expression in nematodes (Zamore et al., *Cell* 101: 25-33, 2000) and in mammalian tissue culture cell lines (Elbashir et al., *Nature* 411: 494-498, 2001). The further therapeutic effectiveness of this approach in mammals was demonstrated in vivo by McCaffrey et al. (*Nature* 418:3 8-39, 2002). The small RNAs are, e.g., at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Such small RNAs that are substantially identical to or complementary to any region of Ang-2 are included in the invention.

Therefore, the invention includes any small RNA substantially identical to at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between) of any region of Ang-2. It should be noted that longer dsRNA fragments can be used that are processed into small RNAs. Useful small RNAs can be identified by their ability to decrease Ang-2 expression levels or biological activity. Small RNAs can also include short hairpin RNAs in which both strands of an siRNA duplex are included within a single RNA molecule.

The specific requirements and modifications of small RNAs are known in the art and are described, for example, in PCT Publication No. WO01/75164 and U.S. Application Publication Numbers 2006/0134787, 2005/0153918, 2005/0058982, 2005/0037988, and 2004/0203145, the relevant portions of which are herein incorporated by reference. In particular embodiments, siRNAs can be synthesized or generated by processing longer double-stranded RNAs, for example, in the presence of the enzyme dicer under conditions in which the dsRNA is processed to RNA molecules of about 17 to about 26 nucleotides. siRNAs can also be generated by expression of the corresponding DNA fragment (e.g., a hairpin DNA construct). Generally, the siRNA has a characteristic 2- to 3-nucleotide 3' overhanging ends, preferably these are (2'-deoxy) thymidine or uracil. The siRNAs typically comprise a 3' hydroxyl group. In some embodiments, single stranded siRNA or blunt-ended dsRNA is used. In order to further enhance the stability of the RNA, the 3' overhangs are stabilized against degradation. In one embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide, is tolerated and does not affect the efficiency of RNAi. The absence of a 2' hydroxyl group significantly enhances the nuclease resistance of the overhang in tissue culture medium.

siRNA molecules can be obtained through a variety of protocols including, e.g., chemical synthesis or recombinant production using a *Drosophila* in vitro system. They can be commercially obtained from companies such as Dharmacon Research Inc. or Xeragon Inc., or they can be synthesized using commercially available kits such as the Silencer™ siRNA Construction Kit from Ambion (Catalog No. 1620) or HiScribe™ RNAi Transcription Kit from New England BioLabs (Catalog No. E2000S).

Alternatively, siRNA can be prepared using standard procedures for in vitro transcription of RNA and dsRNA annealing procedures, such as those described in Elbashir et al. (*Genes Dev.,* 15: 188-200, 2001), Girard et al. (*Nature,* 442: 199-202, 2006), Aravin et al. (*Nature,* 442: 203-207, 2006), Grivna et al., (*Genes Dev.,* 20: 1709-1714, 2006), and Lau et al. (*Science,* 313: 363-367, 2006). siRNAs may also obtained by, e.g., incubation of dsRNA that corresponds to a sequence of the target gene in a cell-free *Drosophila* lysate from syncytial blastoderm *Drosophila* embryos under conditions in which the dsRNA is processed to generate siRNAs of about 21 to about 23 nucleotides, which are then isolated using techniques known to those of skill in the art. For example, gel electrophoresis can be used to separate the 21-23 nucleotide RNAs and the RNAs can then be eluted from the gel slices. In addition, chromatography (e.g., size exclusion chromatography), glycerol gradient centrifugation, and affinity purification with antibodies can be used to isolate the small RNAs.

Short hairpin RNAs (shRNAs), as described in Yu et al. or Paddison et al. (*Proc. Natl. Acad. Sci. USA* 99: 6047-6052, 2002*; Genes Dev.* 16: 948-958, 2002; incorporated herein by reference) can also be used in the methods of the invention. shRNAs are designed such that both the sense and antisense strands are included within a single RNA molecule and connected by a loop of nucleotides (e.g., three or more nucleotides). shRNAs can be synthesized and purified using standard in vitro T7 transcription synthesis as described above and in Yu et al. (supra). shRNAs can also be subcloned into an expression vector that has the mouse U6 promoter sequences, which can then be transfected into cells and used for in vivo expression of the shRNA.

A variety of methods are available for the introduction (e.g., transfection) of dsRNA into mammalian cells. For example, there are several commercially available transfection reagents useful for lipid-based transfection of siRNAs including, but not limited to, TransIT-TKO™ (Mirus, Catalog No. MIR 2150), Transmessenger™ (Qiagen, Catalog No. 301525), Oligofectamine™ and Lipofectamine™ (Invitrogen, Catalog No. MIR 12252-011 and Catalog No. 13778-075), siPORT™ (Ambion, Catalog No. 1631), DharmaFECT™ (Fisher Scientific, Catalog No. T-2001-01). Agents are also commercially available for electroporation-based methods for transfection of siRNA, such as siPORTer™ (Ambion, Catalog No. 1629). Microinjection techniques can also be used. The small RNA can also be transcribed from an expression construct introduced into the cells, where the expression construct includes a coding sequence for transcribing the small RNA operably linked to one or more transcriptional regulatory sequences. Where desired, plasmids, vectors, or viral vectors can also be used for the delivery of dsRNA or siRNA, and such vectors are known in the art. Protocols for each transfection reagent are available from the manufacturer. Additional methods are known in the art and are described, for example in U.S. Patent Application Publication No. 2006/0058255.

Ang-2 Activity Inhibitors

The present invention includes the use of any Ang-2 antagonist compound that reduces or inhibits Ang-2 biological activity (e.g., binding to the Tie-2 receptor, activating Rho kinase, and upregulating MLC phosphorylation) for the treatment of systemic anthrax infections.

Antibodies

Various antibodies are contemplated for use in the therapeutic and diagnostic methods of the present invention. For example, antagonistic antibodies that specifically bind to Ang-2, have a high affinity for Ang-2, and/or neutralize or prevent Ang-2 activity can be used in the therapeutic methods of the present invention. Examples of Ang-2 antibodies include, e.g., L1-7(N), 2Xcon4, L-10 (N), and AB536 (Oliner et al., *Cancer Cell* 6: 507-516, 2004), anti-Ang-2 antibodies from Research Diagnostics Inc. (e.g., Catalog Nos. RDI-ANGIOP2XabR, RDI-ANG218NabG, and RDI-MANGIOP2abrx), and antibodies from AbCam Inc. (e.g., Catalog Nos. Ab 18518, Ab8452, and Ab10601). L1-7(N) is an example of an antibody with high affinity for Ang-2. The $IC_{50}$ for L1-7(N) has been demonstrated to be 0.071 nM for mouse Ang-2, compared to >100 nM for Ang-1.

In addition, anti-Ang-1 agonistic antibodies that function to enhance the activity of Ang-1, for example, by causing Tie-2 phosphorylation or by increasing phosphorylation of the p85 subunit of PI3K, phosphorylation of AKT, activation of Rac1, or activation of p190RhoGAP, are also contemplated by the invention. Antibodies that specifically bind to Tie-2, including but not limited to those that bind to and activate Tie-2 and those that bind to Tie-2 and selectively inhibit binding of Ang-2, but not Ang-1 to the Tie-2 receptor, are also useful in the therapeutic methods of the invention.

Pharmaceutical compositions, for example, including excipients, of any antibodies of the invention are also included. Methods for the preparation and use of antibodies for therapeutic purposes are described in several patents including U.S. Pat. Nos. 6,054,297; 5,821,337; 6,365,157; and 6,165,464 and are incorporated herein by reference. Antibodies can be polyclonal or monoclonal; monoclonal antibodies are preferred.

Monoclonal and Polyclonal Antibodies

Methods for the generation of both monoclonal or polyclonal antibodies may be produced by methods known in the art. These methods include the immunological method described by Kohler and Milstein (*Nature* 256: 495-497, 1975), Kohler and Milstein (*Eur. J. Immunol.* 6: 511-519, 1976), and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (*Science* 246: 1275-1281, 1989).

Human antibodies can also be produced using phage display libraries (Marks et al., *J. Mol. Biol.,* 222: 581-597, 1991 and Winter et al., *Annu. Rev. Immunol.* 12: 433-455, 1994). The techniques of Cole et al. and Boerner et al. are also useful for the preparation of human monoclonal antibodies (Cole et al., supra; Boerner et al., *J. Immunol.* 147: 86-95, 1991).

Monoclonal antibodies are isolated and purified using standard art-known methods. For example, antibodies can be screened using standard art-known methods (e.g., ELISA or Western blot analysis) against an Ang-2 polypeptide or fragment. Non-limiting examples of such techniques are described in Examples II and III of U.S. Pat. No. 6,365,157, herein incorporated by reference.

The antibody may be prepared in any mammal, including, e.g., mice, rats, rabbits, goats, and humans. The antibody may be a member of one of the following immunoglobulin classes: IgG, IgM, IgA, IgD, or IgE, and the subclasses thereof, and preferably is an IgG antibody.

While the preferred animal for producing monoclonal antibodies is mouse, the invention is not so limited; in fact, human antibodies may be used and may prove to be preferable. Such antibodies can be obtained by using human hybridomas (Cole et al., "Monoclonal Antibodies and Cancer Therapy," Alan R. Liss Inc., p. 77-96, 1985).

Monoclonal antibodies, particularly those derived from rodents (e.g., mice) have been used for the treatment of various diseases; however, there are limitations to their use, including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood* 62: 988-995 1983; Schroff et al., *Cancer Res.* 45: 879-885, 1985).

Chimeric Antibodies

The art has attempted to overcome the problem of rodent antibody-induced anti-globulin response by constructing "chimeric" antibodies in which an animal antigen-binding variable domain is coupled to a human constant domain (U.S. Pat. No. 4,816,567; Morrison et al., *Proc. Natl. Acad. Sci. USA* 81: 6851-6855, 1984; Boulianne et al., *Nature* 312: 643-646, 1984; Neuberger et al., *Nature* 314: 268-270, 1985). Chimerized antibodies preferably have constant regions derived substantially or exclusively from human antibody constant regions and variable regions derived substantially or exclusively from the sequence of the variable region from a mammal other than a human.

In the present invention, techniques developed for the production of chimeric antibodies by splicing the genes from a mouse antibody molecule of appropriate antigen specificity together with genes from a human antibody molecule can be used (Morrison et al., *Proc. Natl. Acad. Sci.* 81: 6851-6855, 1984; Neuberger et al., *Nature* 312: 604-608, 1984; Takeda et al., *Nature* 314: 452-454, 1985).

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells (e.g., hybridomas) that express the full-length antibody. The fragments may be used by themselves as antibody equivalents or may be recombined into equivalents, as described above. The DNA deletions and recombinations described in this section may be carried out by known methods, such as those described in the published patent applications listed above.

Humanized Antibodies

Humanized antibodies are chimeric immunoglobulins, immunoglobulin chains or fragments thereof (such as Fv, Fab, Fab', F(ab')$_2$, or other antigen-binding subsequences of antibodies) that contain minimal sequence derived from non-human immunoglobulin. Methods for humanizing non-human antibodies are well known in the art (see, e.g., Vaswani and Hamilton, *Ann. Allergy Asthma Immunol.* 81:105-119, 1998 and Carter, *Nature Reviews Cancer* 1: 118-129, 2001). Generally, a humanized antibody has one or more amino acid residues introduced into it from a source that is non-human. These non-human amino acid residues are often referred to as import residues, which are typically taken from an import variable domain.

Humanization of an antibody can be essentially performed following the methods known in the art (Jones et al., *Nature* 321: 522-525, 1986; Riechmann et al., *Nature* 332: 323-329, 1988; and Verhoeyen et al., *Science* 239: 1534-1536 1988) by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see, for example, U.S. Pat. No. 4,816,567). In practice, humanized antibodies are typically human antibodies in which some CDR residues and possibly some framework residues are substituted by residues from analogous sites in rodent antibodies (Presta, Curr. Op. Struct. Biol. 2: 593-596, 1992).

Additional methods for the preparation of humanized antibodies can be found in U.S. Pat. Nos. 5,821,337, and 6,054, 297, and Carter, (supra), which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Functional Equivalents or Derivatives of Antibodies

The invention also includes functional equivalents or derivatives of the antibodies described in this specification. Functional equivalents or derivatives include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies, antibody fragments, and antibodies, or fragments thereof, fused to a second protein, or fragment thereof. Methods of producing such functional equivalents are disclosed, for example, in PCT Publication No. WO93/21319; EP 0239400; PCT Publication No. WO89/09622; EP 0338745; EP 0332424; and U.S. Pat. No. 4,816,567; each of which is herein incorporated by reference.

Functional equivalents of antibodies also include single-chain antibody fragments, also known as single-chain antibodies (scFvs). Single-chain antibody fragments are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to ensure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

Functional equivalents further include fragments of antibodies that have the same or comparable binding characteristics to those of the whole antibody. Such fragments may contain one or both Fab fragments or the F(ab')$_2$ fragment. Preferably the antibody fragments contain all six CDRs of the whole antibody, although fragments containing fewer than all of such regions, such as three, four or five CDRs, are also functional.

Further, the functional equivalents may be or may combine members of any one of the following immunoglobulin classes: IgG, IgM, IgA, IgD, or IgE, and the subclasses thereof.

Equivalents of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

Purified Proteins

Purified or isolated Ang-1 polypeptides, or fragments thereof, or nucleic acids encoding Ang-1 polypeptides, or fragments thereof, can be used as a therapeutic compound in the methods of the invention. In tumors, Ang-1 binds to and activates the Tie-2 receptor of the PI3K/Akt pathway to promote the survival of endothelial cells (Papapetropoulos et al., Lab Invest. 79: 213-223, 1999, Kim et al., Circ. Res. 86: 24-29, 2000). Ang-1 can also act to upregulate proteins, such as, e.g., VE-cadherins, that stabilize tight inter-endothelial adherens junctions, and that activate Rac1 through PI3K and inhibit RhoA through p190RhoGAP. Any fragment of Ang-1 that can bind to Tie-2 and/or activate Tie-2 signaling (e.g., by receptor phosphorylation, Rac1 activation, p190RhoGAP activation, and/or RhoA inhibition) is included as a preferred fragment of Ang-1 for the therapeutic methods of the invention.

Purified Ang-2 binding proteins that bind to Ang-2 and prevent binding to the Tie-2 receptor can also be used in the methods of the invention. Examples of such Ang-2 binding proteins include, e.g., soluble fragments of Tie-2 that include the extracellular domain of Tie-2 required to bind to Ang-2 or dominant negative forms of Ang-2.

For any of the purified proteins or any fragment thereof, the proteins are prepared using standard methods known in the art. Analogs or homologs which can bind to or block the biological activity of Ang-2 are also included and can be constructed, for example, by making various substitutions of residues or sequences, deleting terminal or internal residues or sequences not needed for biological activity, or adding terminal or internal residues which may enhance biological activity. Amino acid substitutions, deletions, additions, or mutations can be made to improve expression, stability, or solubility of the protein in the various expression systems. Generally, substitutions are made conservatively and take into consideration the effect on biological activity. Mutations, deletions, or additions in nucleotide sequences constructed for expression of analog proteins or fragments thereof must, of course, preserve the reading frame of the coding sequences and preferably will not create complementary regions that could hybridize to produce secondary mRNA structures, such as loops or hairpins, that would adversely affect translation of the mRNA.

Therapeutics that Target the Ang-1/Tie-2 Signaling Pathway

The Tie-2 receptor is primarily expressed on the surface of endothelial cells, though Tie-2 positive bone marrow-derived cells have been described. In tumors, Ang-1 promotes survival of endothelial cells through Tie-2 activation. Ang-1 activation of Tie-2 leads to receptor phosphorylation and subsequence signal transduction that promotes endothelial cell survival and vessel assembly. Ang-1 activates Rac1 through PI3K and inhibits RhoA through p190RhoGAP (see, e.g., PCT/US2006/035582, hereby incorporated by reference). Ang-2 can bind to Tie-2, but is thought to act as an antagonist to the receptor by blocking receptor phosphorylation. However, the action of Ang-2 on the Tie-2 receptor is context, dose, and duration dependent. Ang-2 can block Tie-2 function under physiologic conditions, resulting in a shift in the balance away from Rac1 activation and towards Rho kinase activity which leads to MLC phosphorylation via either activation of endothelial cell MLC kinase or inhibition of myosin phosphatase activity, endothelial cell contraction, and disruption of barrier integrity. Given our identification of the importance of the Ang-2 signaling pathway in the development of inflammation, vascular leak, and thrombosis associated with systemic anthrax infection, any compounds that activate Tie-2 signaling or that block the Ang-2 mediated inactivation of Tie-2 signaling are included as therapeutic compounds of the invention. Such compounds include, for example, compounds that induce Tie-2 biological activity for example by increasing levels of Tie-2, binding to and activating Tie-2, or increasing levels or biological activity of downstream effectors of Tie-2 and include, for example, compounds that inhibit or reduce MLC phosphorylation (e.g., compounds that inhibit Rho kinase activity, such as Y27632, compounds that inhibit endothelial cell MLC kinase activity, such as ML-7, or compounds that activate myosin phosphatase activity), compounds that activate p190RhoGAP, compounds that activate Rac1, and Tie-2 mutants that are constitutively active.

Modifications of Ang-2 Antagonist Compounds

The Ang-2 antagonist compounds of the invention (e.g., polypeptide, antibodies, or small molecule compounds) can also include any modified forms of the compounds of the invention. Examples of post-translational modifications include, but are not limited to, phosphorylation, glycosylation, hydroxylation, sulfation, acetylation, isoprenylation, proline isomerization, subunit dimerization, or multimerization, and cross-linking or attachment to any other proteins, or fragments thereof, or membrane components, or fragments thereof (e.g., cleavage of the protein from the membrane with a membrane lipid component attached). Modifications that provide additional advantages (e.g., increased affinity, decreased off-rate, solubility, stability, and in vivo or in vitro circulating time of the polypeptide, or decreased immunogenicity) include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination are also included (see, e.g., Creighton, "Proteins: Structures and Molecular Properties," 2d Ed., W. H. Freeman and Co., N.Y., 1992; "Posttranslational Covalent Modification of Proteins," Johnson, Ed., Academic Press, New York, 1983; Seifter et al., *Meth. Enzymol.* 182: 626-646, 1990; Rattan et al., *Ann. NY Acad. Sci.* 663: 48-62, 1992). The Ang-2 antagonist compound can also include sequence variants of any of the compounds such as variants that include, e.g., 1, 2, 3, 4, 5, greater than 5, or greater than 10 amino acid alterations, such as, e.g., substitutions, deletions, or insertions with respect to wild-type sequence. Additionally, the Ang-2 antagonist compound may contain one or more non-classical amino acids. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue.

In addition, chemically modified derivatives of the Ang-2 antagonist compounds, which may provide additional advantages such as increased solubility, stability and circulating time of the polypeptide, or decreased immunogenicity are also included (see, e.g., U.S. Pat. No. 4,179,337, hereby incorporated by reference). The chemical moieties for derivitization may be selected from water soluble polymers, such as, for example, polyethylene glycol, ethylene glycol/propylene glycol copolymers, carboxy-methylcellulose, dextran, polyvinyl alcohol, and the like. The Ang-2 antagonist compound may be modified at random positions within the molecule or at predetermined positions within the molecule and may include, e.g., one, two, three, or more attached chemical moieties.

The polymer may be of any molecular weight and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity, and other known effects of the polyethylene glycol to a therapeutic protein or analog). As noted above, the polyethylene glycol may have a branched structure. Branched polyethylene glycols are described, for example, in U.S. Pat. No. 5,643,575;

Morpurgo et al., *Appl. Biochem. Biotechnol.* 56: 59-72, 1996; Vorobjev et al., *Nucleosides Nucleotides* 18: 2745-2750, 1999; and Caliceti et al., *Bioconjug. Chem.* 10: 638-646, 1999, the disclosures of each of which are incorporated by reference.

Any of the Ang-2 antagonist compounds of the present invention (e.g., polypeptides, antibodies, or small molecule compounds) may also be modified in a way to form a chimeric molecule containing an Ang-2 antagonist fused to another, heterologous polypeptide or amino acid sequence, such as, e.g., an Fc sequence, a detectable label, or an additional therapeutic molecule. In one example, an Ang-2 antagonist antibody can be a peptide fused to an Fc fusion protein.

For any of the polypeptides, including antibodies, that are used in the methods of the invention, the nucleic acids encoding the polypeptides or antibodies, or fragments thereof, are also useful in the methods of the invention using standard techniques for gene therapy known in the art and described herein. The invention also includes Ang-2 antagonist compounds (e.g., mimetics) that are based on modeling the three-dimensional structure of a polypeptide or peptide fragment and using rational drug design to provide potential inhibitor compounds with particular molecular shape, size, and charge characteristics. Following identification of an Ang-2 antagonist compound, suitable modeling techniques known in the art can be used to study the functional interactions and to design mimetic compounds which contain functional groups arranged in such a manner that they could reproduce those interactions. The designing of mimetics to a known pharmaceutically active compound is a known approach to the development of pharmaceuticals based on a lead compound. This might be desirable where the active compound is difficult or expensive to synthesize or where it is unsuitable for a particular method of administration (e.g., peptides not suitable as active agents for oral compositions due to degradation by proteases in the alimentary canal). Mimetic design, synthesis, and testing may be used to avoid randomly screening large numbers of molecules for a target property. The mimetic or mimetics can then be screened to see whether they reduce or inhibit Ang-2 biological activity, and further optimization or modification can then be carried out to arrive at one or more final mimetics for in vivo or clinical testing.

Combination Therapies for the Treatment of Systemic Anthrax Infections

In various embodiments Ang-2 antagonists can be provided in conjunction (e.g., before, during, or after) with additional therapies to treat a systemic anthrax infection. Treatment therapies that can be used in combination with the methods of the invention include, but are not limited to, antibiotics (e.g., fluoroquinolones (e.g., ciprofloxacin, doxycycline, erythromycin, vancomycin, or penicillin)), surgical drainage of infected fluid collections, fluid replacement, and appropriate support for organ dysfunction, including, for example, hemodialysis in kidney failure, mechanical ventilation in pulmonary dysfunction, transfusion of blood plasma, platelets, and coagulation factors to stabilize blood coagulation, and drug and fluid therapy for circulatory failure. An additional therapy may include administration of activated protein C or recombinant activated protein C (e.g., drotrecogin alpha). Alternatively, treatment of the systemic anthrax infection of a subject may be accompanied by administration of an anthrax vaccine (e.g., Anthrax Vaccine Adsorbed (AVA) manufactured by BioPort Co.) for the prevention of subsequent anthrax infections.

Desirably, Ang-2 antagonist compounds can be formulated alone or in combination with any additional therapies, either described herein or known in the art. A combination of any two or more of the Ang-2 antagonist compounds described herein can also be used for the treatment of a systemic anthrax infection. In one example, an Ang-2 antagonist compound that specifically blocks Ang-2 activity (e.g., an Ang-2 antibody) is combined with a compound that is an antagonist of Ang-2 or Tie-2 (e.g., an isolated Ang-1 fragment that binds Tie-2 and prevents Ang-2 from binding to Tie-2) or that shifts the cellular balance towards p190RhoGAP activation and away from RhoA activation.

Other therapies useful in the treatment of a systemic anthrax infection are described, for example, in U.S. Pat. Nos. 6,436,933, 6,569,630, 6,913,756, and 7,282,580, hereby incorporated by reference. Therapies useful in treating vascular leak, a symptom that may be associated with a systemic anthrax infection, are described in PCT/US2006/035582, hereby incorporated by reference.

Therapeutic Formulations

The dosage and the timing of administering the Ang-2 antagonist compound of the invention depend on various clinical factors including the overall health of the subject and the severity of the symptoms of the systemic anthrax infection. The invention includes the use of Ang-2 antagonists to treat, inhibit, or prevent systemic anthrax infections. The Ang-2 antagonist can be administered at anytime (e.g., after diagnosis or detection of a systemic anthrax infection or a condition associated with systemic anthrax infection (e.g., using the diagnostic methods known in the art or described herein), after exposure to anthrax bacilli in subjects that have not yet been diagnosed with a systemic anthrax infection but are at risk of developing such a disorder (e.g., subjects suffering from or being treated for symptoms associated with systemic anthrax infection), or after a risk of developing a systemic anthrax infection is determined.

The Ang-2 antagonist compounds of the present invention can be formulated and administered in a variety of ways (e.g., routes known for specific indications, including, but not limited to, topically, orally, subcutaneously, bronchial injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly). For example, the Ang-2 antagonist compound can be in the form of a pill, tablet, capsule, liquid, or sustained-release tablet for oral administration; a liquid for intravenous, subcutaneous or administration; a polymer or other sustained-release vehicle for local administration; or an ointment, cream, gel, liquid, or patch for topical administration.

For example, continuous systemic infusion or periodic injection of the Ang-2 antagonist compound can be used to treat or prevent a systemic anthrax infection. Treatment can be continued for a period of time ranging from one day through the lifetime of the subject, more preferably 1 to 100 days, and most preferably 1 to 60 days and most preferably, until the symptoms of systemic anthrax infection are reduced or removed or until diagnostic tests demonstrate the absence of the bacilli in the subject's serum (e.g., blood). Dosages vary depending on the compound and the severity of the condition. The Ang-2 antagonist compounds can be administered continuously by infusion, using a constant- or programmable-flow implantable pump, or by periodic injections. Sustained-release systems can also be used. Semipermeable, implantable membrane devices are also useful as a means for delivering Ang-2 antagonists in certain circumstances. In another embodiment, the Ang-2 antagonist compound is administered locally, e.g., by inhalation, and can be repeated periodically.

Therapeutic formulations are prepared using standard methods known in the art by mixing the active ingredient having the desired degree of purity with optional physiologically acceptable carriers, excipients, or stabilizers in the form of lyophilized formulations or aqueous solutions (Remington's Pharmaceutical Sciences ($20^{th}$ edition), Ed. A. Gennaro, 2000, Lippincott, Williams & Wilkins, Philadelphia, Pa.). Acceptable carriers include, e.g., saline; buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagines, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at physiological concentrations. Optionally, the formulations of the invention can contain a pharmaceutically acceptable preservative. In some embodiments, the preservative concentration ranges from 0.1 to 2.0% v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween-20 and pluronic acid (F68). Suitable surfactant concentrations are, e.g., 0.005 to 0.02%.

The dosage of the Ang-2 antagonistic compound will depend on other clinical factors, such as the weight and condition of the subject and the route of administration of the compound. For treating subjects, between approximately 0.1 mg/kg to 500 mg/kg body weight of the Ang-2 antagonistic compound can be administered. A more preferable range is 1 mg/kg to 50 mg/kg body weight with the most preferable range being from 1 mg/kg to 25 mg/kg body weight. Depending upon the half-life of the Ang-2 antagonistic compound in the particular subject, the Ang-2 antagonistic compound can be administered 1, 2, 3, 4, or 5 times per day, 1, 2, 3, 4, 5, or 6 times per week, once every two weeks, once a month, or more or less frequently. The methods of the present invention provide for single as well as multiple administrations, given either simultaneously or over an extended period of time.

If antibodies are used in vivo for the treatment or prevention of systemic anthrax infection, the antibodies of the invention are administered to the subject in therapeutically effective amounts. Preferably, the antibodies are administered parenterally or intravenously by continuous infusion. The dose and dosage regimen depends upon the severity of the disease and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (e.g., solution, suspension, or emulsion) in association with a pharmaceutically acceptable parenteral vehicle. Such vehicles are inherently nontoxic, and non-therapeutic. Examples of such vehicles are, e.g., water, saline, Ringer's solution, dextrose solution, and 5% human serum albumin. Nonaqueous vehicles, such as fixed oils and ethyl oleate, may also be used. Liposomes may be used as carriers. The vehicle may contain minor amounts of additives, such as substances that enhance isotonicity and chemical stability (e.g., buffers and preservatives). The antibodies typically are formulated in such vehicles at concentrations of about 1 mg/ml to 10 mg/ml.

The dosage required depends on the choice of the route of administration; the nature of the formulation; the nature of the subject's illness; the subject's size, weight, surface area, age, and sex; other drugs being administered; and the judgment of the attending physician. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization, as is well understood in the art. Administrations can be single or multiple (e.g., 2-, 3-, 6-, 8-, 10-, 20-, 50-, 100-, 150-, or more administrations). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding an Ang-2 antagonist can be delivered to the appropriate cells in the subject. Expression of the coding sequence can be directed to any cell in the body of the subject. In certain embodiments, expression of the coding sequence can be directed to the lung. This can be achieved by, for example, the use of polymeric, biodegradable microparticle, or microcapsule delivery devices known in the art.

The nucleic acid can be introduced into the cells by any means appropriate for the vector employed. Many such methods are well known in the art (Sambrook et al., supra, and Watson et al., Recombinant DNA, Chapter 12, 2d edition, Scientific American Books, 1992). Examples of methods of gene delivery include, e.g., liposome-mediated transfection, electroporation, calcium phosphate/DEAE dextran methods, gene gun, and microinjection.

In gene therapy applications, genes are introduced into cells in order to achieve in vivo synthesis of a therapeutically effective genetic product. "Gene therapy" includes both conventional gene therapy, where a lasting effect is achieved by a single treatment, and the administration of gene therapeutic agents, which involves the one-time or repeated administration of a therapeutically effective DNA or mRNA. Standard gene therapy methods typically allow for transient protein expression at the target site ranging from several hours to several weeks. Re-application of the nucleic acid can be utilized as needed to provide additional periods of expression of Ang-2 antagonist compounds.

Another way to achieve uptake of the nucleic acid is using liposomes, which may be prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al., *J. Mol. Med.* 73: 479, 1995). Alternatively, tissue-specific targeting can be achieved by the use of tissue-specific transcriptional regulatory elements which are known in the art. Delivery of "naked DNA" (i.e., without a delivery vehicle) to an intramuscular, intradermal, or subcutaneous site is another means to achieve in vivo expression.

Gene delivery using viral vectors (e.g., adenoviral, retroviral, lentiviral, or adeno-associated viral vectors) can also be used. Numerous vectors useful for this purpose are generally known and have been described (Miller, *Human Gene*

Therapy 15: 14, 1990; Friedman, Science 244: 1275-1281, 1989; Eglitis and Anderson, BioTechniques 6: 608-614, 1988; Tolstoshev and Anderson, Current Opinion in Biotechnology 1: 55-61, 1990; Sharp, The Lancet 337: 1277-1278, 1991; Cornetta et al., Nucleic Acid Research and Molecular Biology 36: 311-322, 1987; Anderson, Science 226: 401-409, 1984; Moen, Blood Cells 17: 407-416, 1991; Miller and Rosman, Biotechniques 7: 980-990, 1989; Rosenberg et al., N Engl. J. Med 323: 370, 1990, Groves et al., Nature, 362: 453-457, 1993; Horrelou et al., Neuron, 5: 393-402, 1990; Jiao et al., Nature 362: 450-453, 1993; Davidson et al., Nature Genetics 3: 2219-2223, 1993; Rubinson et al., Nature Genetics 33: 401-406, 2003; U.S. Pat. Nos. 6,180,613; 6,410,010; 5,399, 346, all hereby incorporated by reference). These vectors include, e.g., adenoviral vectors and adeno-associated virus-derived vectors, retroviral vectors (e.g., Moloney murine leukemia virus-based vectors, spleen necrosis virus-based vectors, Friend murine leukemia-based vectors, lentivirus-based vectors (Lois et al., Science 295: 868-872, 2002; Rubinson et al., supra), papova virus-based vectors (e.g., SV40 viral vectors), herpes virus-based vectors, viral vectors that contain or display the vesicular stomatitis virus glycoprotein spike, Semliki-Forest virus-based vectors, hepadnavirus-based vectors, and baculovirus-based vectors.

In the relevant polynucleotides (e.g., expression vectors), the nucleic acid sequence encoding the Ang-2 antagonistic polypeptide (including an initiator methionine and optionally a targeting sequence) is operatively linked to a promoter or enhancer-promoter combination. Short amino acid sequences can act as signals to direct proteins to specific intracellular compartments. Such signal sequences are described in detail in, e.g., U.S. Pat. No. 5,827,516, incorporated herein by reference in its entirety.

An ex vivo strategy can also be used for therapeutic applications. Ex vivo strategies involve transfecting or transducing cells obtained from the subject with a polynucleotide encoding an Ang-2 antagonistic polypeptide. The transfected or transduced cells are then returned to the subject. Such cells act as a source of the Ang-2 antagonistic polypeptide for as long as they survive in the subject.

The ex vivo methods include the steps of, e.g., harvesting cells from a subject, culturing the cells, transducing them with an expression vector, and maintaining the cells under conditions suitable for expression of the Ang-2 antagonistic polypeptide or functional fragment. These methods are known in the art of molecular biology. The transduction step is accomplished by any standard means used for ex vivo gene therapy including, e.g., calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the patient.

Where sustained release administration of Ang-2 antagonist is desired in a formulation with release characteristics suitable for the treatment of any disease or disorder requiring administration of the Ang-2 antagonist, microencapsulation of the Ang-2 antagonist is contemplated. Microencapsulation of recombinant proteins for sustained release has been successfully performed with human growth hormone (rhGH), interferon-(rhIFN-), interleukin-2, and MN rgp120 (Johnson et al., Nat. Med. 2: 795-799, 1996; Yasuda, Biomed. Ther. 27: 1221-1223, 1993; Hora et al., Bio/Technology 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference).

The sustained-release formulations may include those developed using poly-lactic-coglycolic acid (PLGA) polymer. The degradation products of PLGA, lactic and glycolic acids, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990).

The Ang-2 antagonist for use in the present invention may also be modified in a way to form a chimeric molecule comprising one Ang-2 antagonist fused to another heterologous polypeptide or amino acid sequence, such as an Fc sequence or an additional therapeutic molecule (e.g., an antibiotic).

The Ang-2 antagonist compound can be packaged alone or in combination with other therapeutic compounds as a kit. Non-limiting examples include, e.g., kits that contain, e.g., one pill, two pills, a powder (optionally in combination with a pill or tablet), a suppository and a liquid in a vial, or two topical creams.

The kit can include optional components that aid in the administration of the unit dose to patients, such as vials for reconstituting powder forms, syringes for injection, customized IV delivery systems, or inhalers. Additionally, the unit dose kit can contain instructions for preparation and administration of the compositions. The kit may be manufactured as a single-use unit dose for one subject, multiple uses for a particular subject (at a constant dose or in which the individual compounds may vary in potency as therapy progresses), or the kit may contain multiple doses suitable for administration to multiple subjects ("bulk packaging"). The kit components may be assembled in cartons, blister packs, bottles, tubes, or vials.

Diagnostics

We have shown that Ang-2 levels are elevated in subjects infected with systemic anthrax and that measurement of Ang-2 levels can be used as a tool to diagnose or predict the severity of a systemic anthrax infection of a subject.

The present invention features methods and compositions to treat, diagnose, and stratify subjects exposed to or infected with the anthrax bacilli using Ang-2 nucleic acid molecules and polypeptides as indicators of infection. The methods and compositions can include the measurement of Ang-2 polypeptides, either free or bound to another molecule, or any fragments or derivatives thereof. The methods can include measurement of absolute levels of Ang-2 or relative levels as compared to a normal reference. For example, a serum level of Ang-2 that is less than 5 ng/ml, 4 ng/ml, 3 ng/ml, 2 ng/ml, or less than 1 ng/ml serum is considered to be predictive of a low risk of systemic anthrax infection or of a good outcome in a patient diagnosed with a systemic anthrax infection syndrome. A serum level of Ang-2 that is greater than 5 ng/ml, 10 ng/ml, 20 ng/ml, 30 ng/ml, 40 ng/ml, or 50 ng/ml is considered diagnostic of systemic anthrax infection or of a poor outcome in a subject already diagnosed with an infection.

For diagnoses based on relative levels of Ang-2, a subject with a systemic anthrax infection will show an alteration (e.g., an increase of 10%, 20%, 30%, 40%, 50%, 60%, 70%, 80%, 90%, or more) in the expression of an Ang-2 polypeptide as compared to a normal reference sample or level. A normal reference sample can be, for example, a prior sample taken from the same subject prior to the development of the infection or of symptoms suggestive of systemic anthrax infection, a sample from a subject not having any infection, a sample from a subject not having sepsis or vascular leak associated with increased levels of Ang-2, or a sample of a purified reference polypeptide at a known normal concentration (i.e., not indicative of systemic anthrax infection). By "reference standard or level" is meant a value or number derived from a reference sample. A normal reference standard or level can be a value or number derived from a normal subject.

For diagnostic assays that include measuring the amount of Ang-2 polypeptide, the Ang-2 polypeptide can include full-length Ang-2 polypeptide, degradation products, alternatively spliced isoforms of Ang-2 polypeptide, enzymatic cleavage products of Ang-2 polypeptide, and the like. In one example, an antibody that specifically binds Ang-2 polypeptide is used for the diagnosis of a systemic anthrax infection or to provide a prognosis for a subject already suffering from such an infection.

Standard methods may be used to measure levels of Ang-2 polypeptide in any cell, tissue, or bodily fluid, including, but not limited to, urine, blood, serum, plasma, saliva, amniotic fluid, or cerebrospinal fluid. Such methods include immunoassay, ELISA, Western blotting using antibodies that specifically bind to Ang-2 polypeptide, and quantitative enzyme immunoassay techniques. ELISA assays are the preferred method for measuring levels of Ang-2 polypeptide. Increases in the levels of Ang-2 polypeptide, as compared to normal controls, are considered a positive indicator of a systemic anthrax infection or a poor prognosis in a subject already suffering from such an infection.

Ang-2 nucleic acid molecules, or substantially identical fragments thereof, or fragments or oligonucleotides of Ang-2 that hybridize to Ang-2 at high stringency may be used as a probe to monitor expression of Ang-2 nucleic acid molecules in the diagnostic methods of the invention. Increases in the levels of Ang-2 nucleic acid molecules, as compared to normal controls, are considered a positive indicator of systemic anthrax infection or a poor prognosis in a subject already suffering from such an infection.

In one embodiment, a subject having a systemic anthrax infection will show an increase in the expression of a nucleic acid encoding Ang-2 or an increase in Ang-2 polypeptide levels. Methods for detecting such alterations are standard in the art and are described in Ausubel et al., supra. In one example, Northern blotting or PCR (e.g., RT-PCR or real-time) is used to detect Ang-2 mRNA levels.

In another embodiment, hybridization at high stringency with PCR probes that are capable of detecting an Ang-2 nucleic acid molecule, including genomic sequences or closely related molecules, may be used to hybridize to a nucleic acid sequence derived from a subject having a systemic anthrax infection. The specificity of the probe, whether it is made from a highly specific region, e.g., the 5' regulatory region, or from a less specific region, e.g., a conserved motif, and the stringency of the hybridization or amplification (e.g., maximal, high, intermediate, or low) determine whether the probe hybridizes to a naturally occurring sequence, allelic variants, or other related sequences. Hybridization techniques may be used to monitor expression levels of a gene encoding an Ang-2 polypeptide (for example, by Northern analysis, Ausubel et al., supra).

In one embodiment, the level of Ang-2 polypeptide or nucleic acid, or any combination thereof, is measured at least two different times and an alteration in the levels (e.g., increase by 10%, 20%, 30%, 40%, 50%, 60%, 70%, 80%, 90%, or more) over time is used as an indicator of a systemic anthrax infection. For example, serum samples can be taken at regular intervals (e.g., every 2 hours, 4 hours, 6 hours, 8 hours, 12 hours, 24 hours, every two days, or more or less frequently) to determine the level of Ang-2 polypeptide or nucleic acid. If the level of Ang-2 increases over the serial measurements, this is considered a diagnostic indicator of a systemic anthrax infection, or, if the subject is already determined to have such an infection, this is considered to be an indicator of a poor prognosis.

The diagnostic methods described herein can be used individually or in combination with any other diagnostic method described herein for a more accurate diagnosis of the presence or severity of a systemic anthrax infection. In additional preferred embodiments, other known diagnostic methods for systemic anthrax infection can be used in combination with the methods described herein. Examples of additional methods for diagnosing systemic anthrax infection include, e.g., examining subject's history of exposure (e.g., contact with a white powder or contact with infected animals or humans), evidence of systemic inflammation (e.g., the presence of fever, tachypnea, or tachycardia), detection of the anthrax protective antigen (PA) using anti-PA IgG detection by ELISA, PCR analyses (e.g., in compliance with the Laboratory Response Network), immunohistochemical staining of tissues, MacFaydean polychrome methylene blue staining of serum (e.g., blood) for the detection of anthrax bacilli, chest x-rays (e.g., to detect mediastinal widening, pleural effusion, or infiltrates), computed tomography (CT) scans (e.g., to detect mesenteric adenopathy), or culture growths.

Diagnostic Kits

The invention also provides for a diagnostic test kit. For example, a diagnostic test kit can include antibodies that specifically bind to Ang-2 polypeptide and components for detecting and, more preferably, evaluating binding between the antibodies and the Ang-2 polypeptide. For detection, either the antibody or the Ang-2 polypeptide is labeled and either the antibody or the Ang-2 polypeptide is substrate-bound, such that the Ang-2 polypeptide-antibody interaction can be established by determining the amount of label attached to the substrate following binding between the antibody and the Ang-2 polypeptide. ELISA is a common, art-known method for detecting antibody-substrate interactions and can be provided with the kit of the invention. Ang-2 polypeptides can be detected in virtually any bodily fluid, such as, e.g., urine, plasma, blood serum, semen, or cerebrospinal fluid. A kit that determines an alteration in the level of Ang-2 polypeptide relative to a reference, such as the level present in a normal control, is useful as a diagnostic kit in the methods of the invention. The kit can also contain a standard curve or a reference level or sample indicating levels of Ang-2 that fall within the normal range and levels that would be considered diagnostic of systemic anthrax infection. Desirably, the kit will contain instructions for the use of the kit. In one example, the kit contains instructions for the use of the kit for the diagnosis of a systemic anthrax infection. In yet another example, the kit contains instructions for the use of the kit to monitor therapeutic treatment or dosage regimens. The kit may also contain other diagnostics useful in diagnosing systemic anthrax infection, or may be used in combination with known anthrax diagnostic measures.

Subject Monitoring

The diagnostic methods described herein can also be used to monitor systemic anthrax infections during therapy or to determine the dosages of therapeutic compounds. In one embodiment, the levels of Ang-2 polypeptide are measured repeatedly as a method of not only diagnosing systemic anthrax infections but also monitoring the treatment, or management of the infection. In order to monitor the progression of a systemic anthrax infection in a subject, subject samples can be obtained at several time points and may then be compared. For example, the diagnostic methods can be used to monitor subjects during antibiotic therapy. In this example, serum samples from a subject can be obtained before treatment with an antibiotic, again during treatment with an antibiotic, and again after treatment with an antibiotic. In this example, the level of Ang-2 polypeptide in a subject is closely monitored and, if the level of Ang-2 polypeptide begins to increase during therapy, the therapeutic regimen for treatment of a systemic anthrax infection can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the infection.

Screening Assays

As discussed above, we have discovered that increased levels of Ang-2 can be used to diagnose systemic anthrax infections and may contribute to the pathogenesis of the infection. Based on these discoveries, compositions of the invention are useful for the high-throughput, low-cost screening of candidate compounds to identify compounds that modulate, preferably by decreasing (e.g., by at least 10%, 20%, 30%, 40%, 50%, 60%, 70%, 80%, 90%, 95%, or more), the expression or biological activity of Ang-2 for the treatment of a systemic anthrax infection.

Any number of methods is available for carrying out screening assays to identify new candidate compounds that modulate (e.g., decrease) the expression of an Ang-2 nucleic acid molecule. In one working example, candidate compounds are added at varying concentrations to the culture medium of cultured cells expressing an Ang-2 nucleic acid sequence. Gene expression is then measured (e.g., by microarray analysis, Northern blot analysis (Ausubel et al., *Current Protocols in Molecular Biology*, Wiley Interscience, New York, 2001), or RT-PCR) using any appropriate fragment prepared from the nucleic acid molecule as a hybridization probe. The level of gene expression in the presence of the candidate compound is compared to the level measured in a control culture medium lacking the candidate compound. A compound that promotes an alteration (e.g., decrease) in the expression of an Ang-2 gene, nucleic acid molecule, or polypeptide, or a functional equivalent thereof, is considered useful in the invention. Such a molecule may be used, for example, as a therapeutic to delay, ameliorate, or treat a systemic anthrax infection in a subject.

In another example, an Ang-2 nucleic acid is expressed as a transcriptional or translational fusion with a detectable reporter in an isolated cell (e.g., mammalian or insect cell) under the control of a heterologous promoter (e.g., an inducible promoter). The cell expressing the fusion protein is then contacted with a candidate compound and the expression of the detectable reporter in that cell is compared to the expression of the detectable reporter in an untreated control cell. A candidate compound that decreases the expression of an Ang-2 detectable reporter fusion is a compound that is useful as a therapeutic to delay, ameliorate, or treat a systemic anthrax infection in a subject. In preferred embodiments, the candidate compound alters the expression of a reporter gene fused to a nucleic acid or nucleic acid.

In another example, the effect of candidate compounds may be measured at the level of polypeptide expression using the same general approach and standard immunological techniques, such as, e.g., Western blotting or immunoprecipitation with an antibody specific for an Ang-2 polypeptide. For example, immunoassays may be used to detect or monitor the expression of at least one of the polypeptides of the invention in an organism. Polyclonal or monoclonal antibodies that are capable of binding to such a polypeptide may be used in any standard immunoassay format (e.g., ELISA, Western blot, or RIA assay) to measure the level of the polypeptide. In some embodiments, a compound that promotes an alteration (e.g., decrease) in the expression or biological activity of an Ang-2 polypeptide is considered particularly useful. Again, such a molecule may be used, for example, as a therapeutic to delay, ameliorate, or treat a systemic anthrax infection in a subject.

In yet another example, candidate compounds may be screened for those that specifically bind to an Ang-2 polypeptide or an Ang-2 receptor such as Tie-2. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind to an Ang-2 polypeptide or bind to and antagonize the Tie-2 receptor.

In yet another example, candidate compounds may be screened for those that specifically modulate Ang-1 function. Preferred candidate compounds will increase (e.g., by at least 10%, 20%, 30%, 40%, 50%, 60%, 70%, 80%, 90%, or more) Ang-1 biological activity. Ang-1 biological activity can be readily assayed using any of the assays known in the art or described herein, including, but not limited to, assays for PI3K activity or p85 subunit phosphorylation, assays for Rac1 activation, assays for p190RhoGAP activation, and assays for RhoA inhibition.

In one particular example, a candidate compound that binds to an Ang-2 polypeptide may be identified using a chromatography-based technique. For example, a recombinant Ang-2 may be purified by standard techniques from cells engineered to express Ang-2 and may be immobilized on a column. A solution of candidate compounds is then passed through the column and a compound specific for the Ang-2 polypeptide is identified on the basis of its ability to bind to the polypeptide and be immobilized on the column. To isolate the compound, the column is washed to remove non-specifically bound molecules and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to decrease the biological activity of an Ang-2 polypeptide. Compounds isolated by this approach may also be used, for example, as therapeutics to treat a systemic anthrax infection in a human subject. Compounds that are identified as binding to Ang-2 or Tie-2 with an affinity constant less than or equal to 10 mM are considered particularly useful in the invention. Alternatively, any in vivo protein interaction detection system, for example, any two-hybrid assay, may be utilized to identify compounds or proteins that bind to a polypeptide of the invention.

Identification of New Compounds or Extracts

In general, compounds capable of decreasing the activity of Ang-2 are identified from large libraries of both natural product or synthetic (or semi-synthetic) extracts of chemical libraries or polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to increase the biological activity of an Ang-2 polypeptide or to bind to an Ang-2 polypeptide, further fractionation of the positive lead extract is necessary to isolate chemical constituents responsible for the observed effect. Thus, the goal of the extraction, fractionation, and purification process is the careful characterization and identification of a chemical entity within the crude extract that decreases the biological activity of an Ang-2 polypeptide. Methods of fractionation and purification of such heterogeneous extracts are known in the art. If desired, compounds shown to be useful as therapeutics for the treatment or prevention of a systemic anthrax infection are chemically modified according to methods known in the art.

EXAMPLES

The examples below demonstrate that anthrax infection results in the elevation of Ang-2 levels in serum (e.g., blood) in an infected subject. This elevation of Ang-2 levels occurs early after infection and persists for the first 1-48 hours post-infection and subsides in those subjects that survive the bacterial challenge. Further, the magnitude of the increase of circulating Ang-2 correlates with the initial dose of the anthrax bacilli that infects the subject. The results suggest that increased Ang-2 levels may be pathogenic, resulting in inflammation, vascular leak, and thrombosis associated with systemic anthrax infections. In sum, these results suggest a causal role for Ang-2 in systemic anthrax infections and a diagnostic utility for Ang-2 in the identification of such infections. Taken together, the results identify Ang-2 as both a biomarker and mediator of systemic anthrax infection. In addition, the examples suggest that Ang-2 antagonists, including, but not limited to, Ang-1, protects against system anthrax infections.

Example 1

Ang-2 Expression in *Bacillus anthracis*-Infected Animal Models

In this example, we demonstrate the elevation of Ang-2 in the serum of baboons infected with the anthrax bacilli.

Baboons were intravenously administered with $6\times10^9$ colony-forming units (CFU) per kilogram of body weight (CFU/kg), $1\times10^9$ CFU/kg, $5\times10^6$ CFU/kg, or $5\times10^5$ CFU/kg of an attenuated version of the anthrax bacilli known as the Sterne strain, typically used in the preparation of a live, attenuated vaccine to inoculate livestock. The Sterne strain produces the major anthrax toxins (including anthrax lethal factor, edema factor, and protective antigen), but is susceptible to complement-mediated killing. Blood from the infected baboons was collected at specific time points (see FIGS. 1-6). The baboon receiving the highest dose of $6\times10^9$ CFU/kg of the bacteria died within the first day. The baboon inoculated with $1\times10^9$ CFU/kg of the bacteria lived until day three of the study, while the other two survived past seven days, indicating clearance of the infection.

Figure 1:
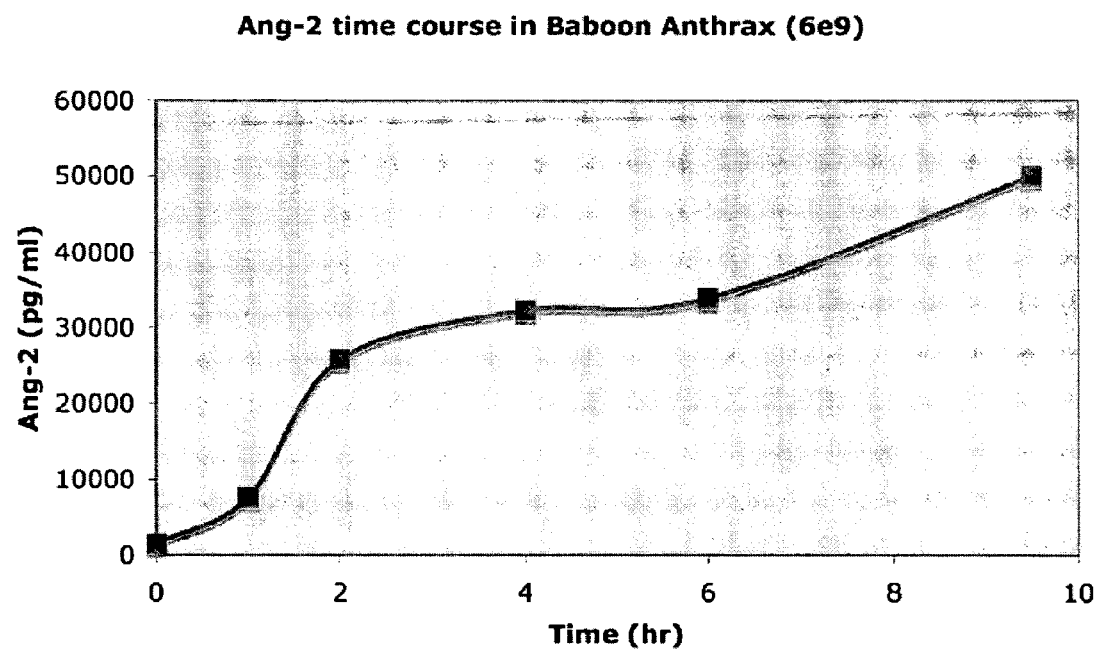
Figure 2:
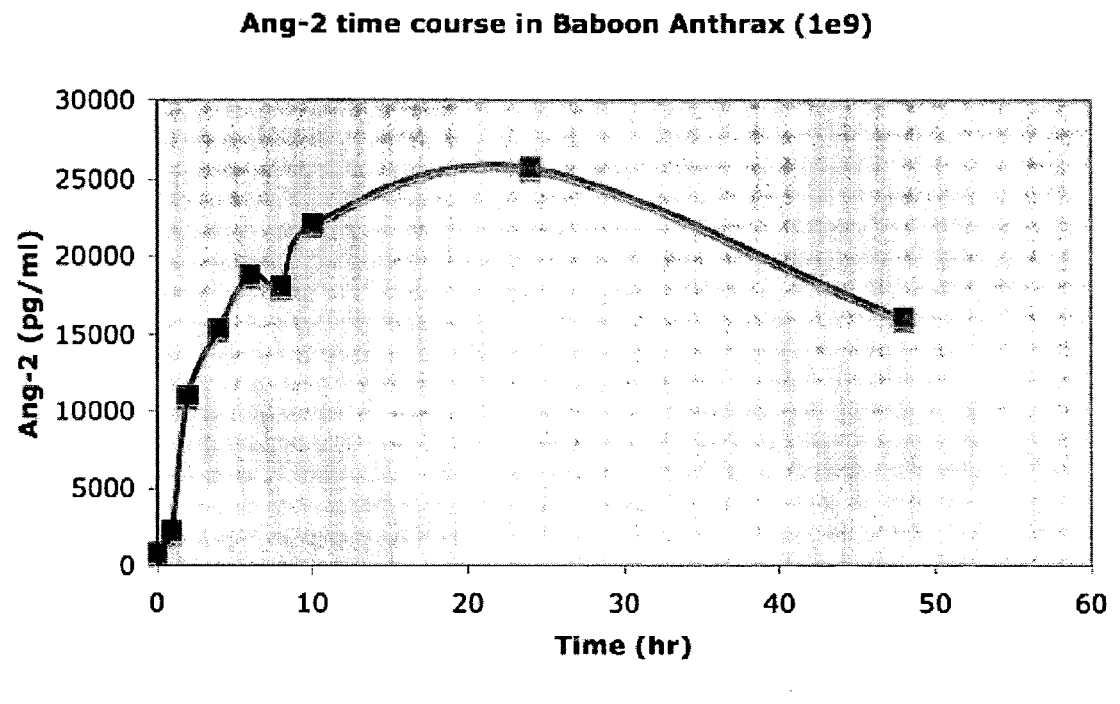
Figure 3:
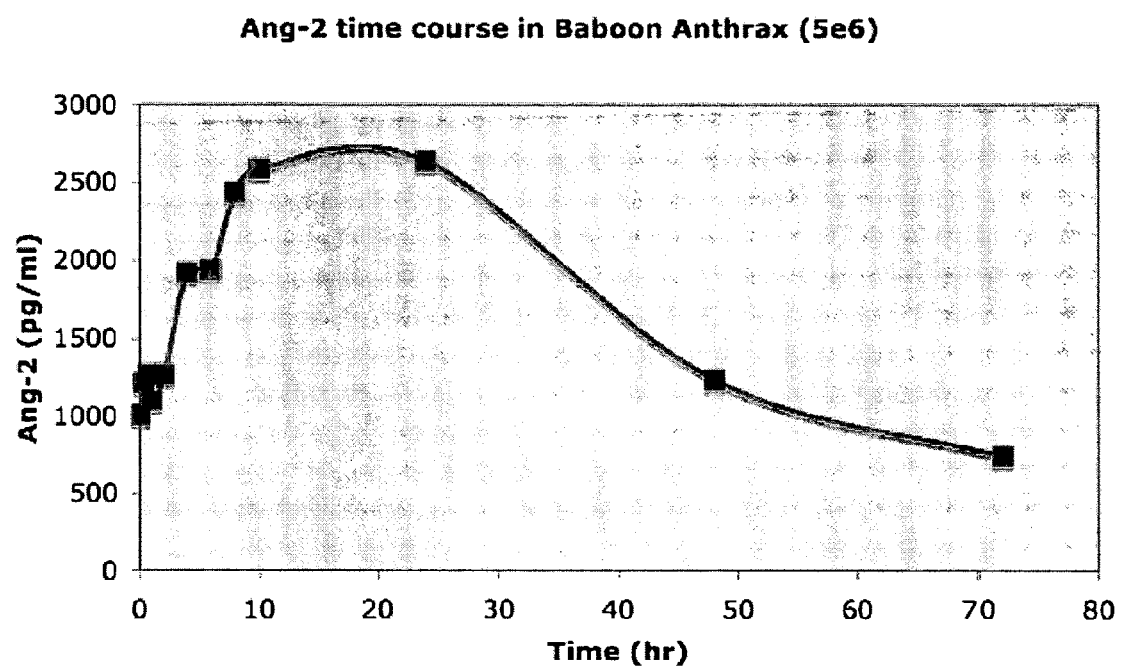
Figure 4:
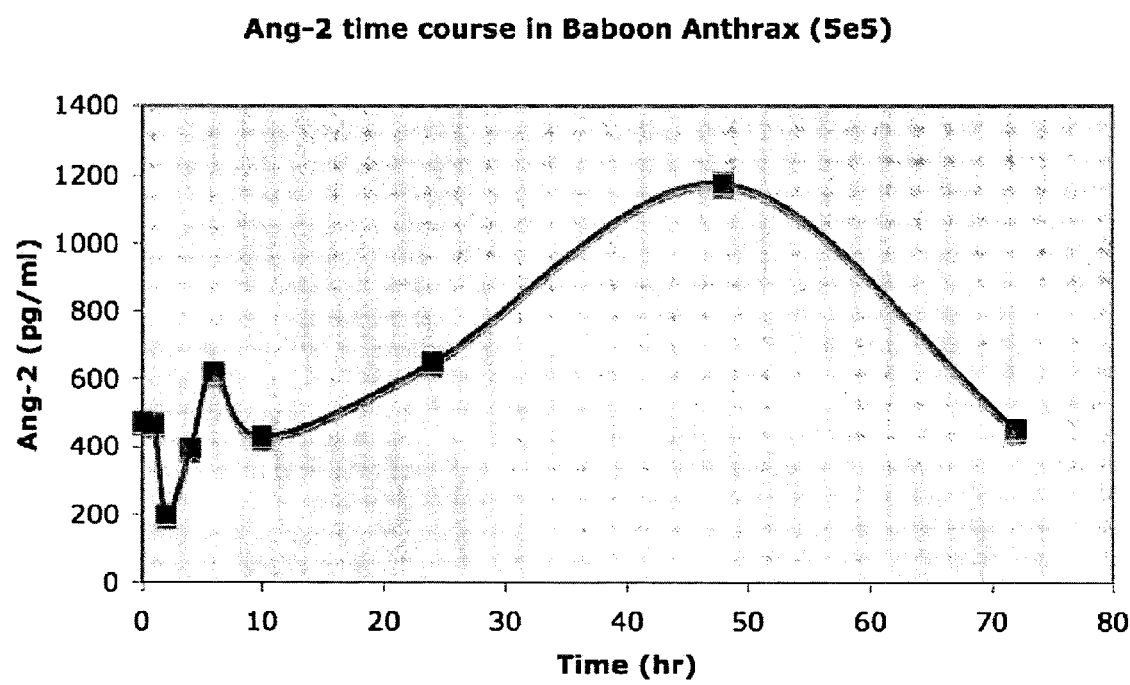
Figure 5:
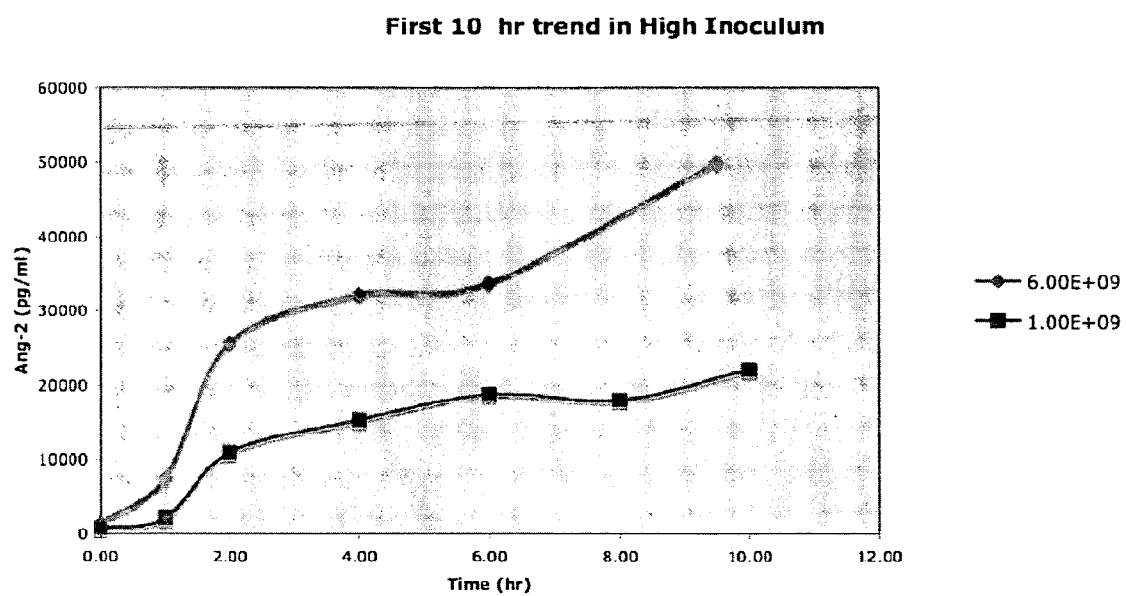
Figure 6:
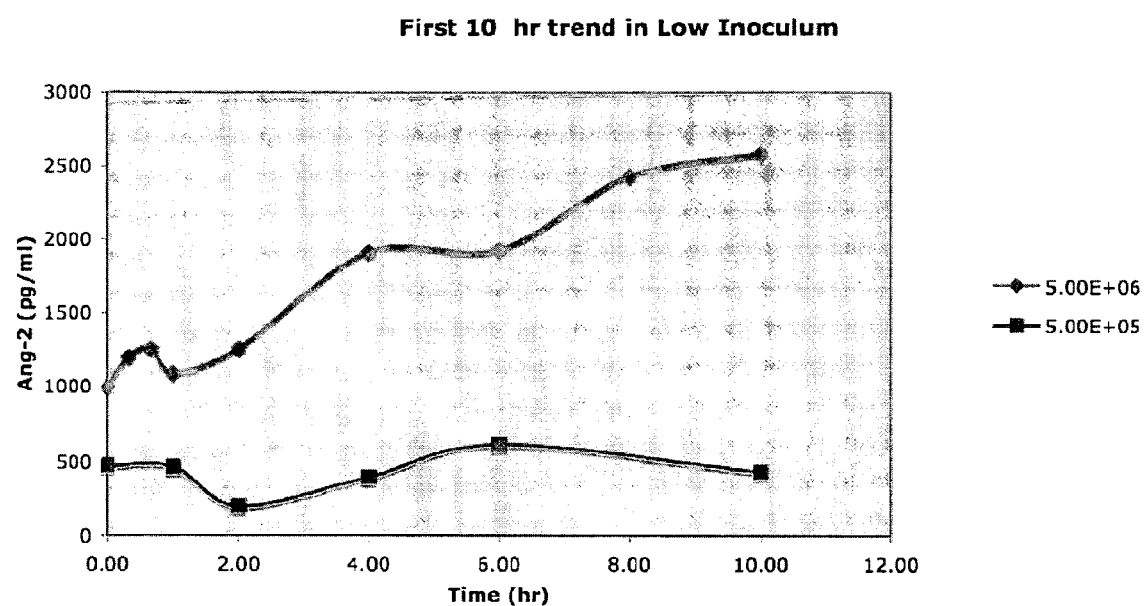
FIG. 6 shows elevation of Ang-2 levels over a ten-hour time period in baboons infected with $5 \times 10^6$ and $5 \times 10^5$ CFU/kg of anthrax bacilli.
Figure 7:
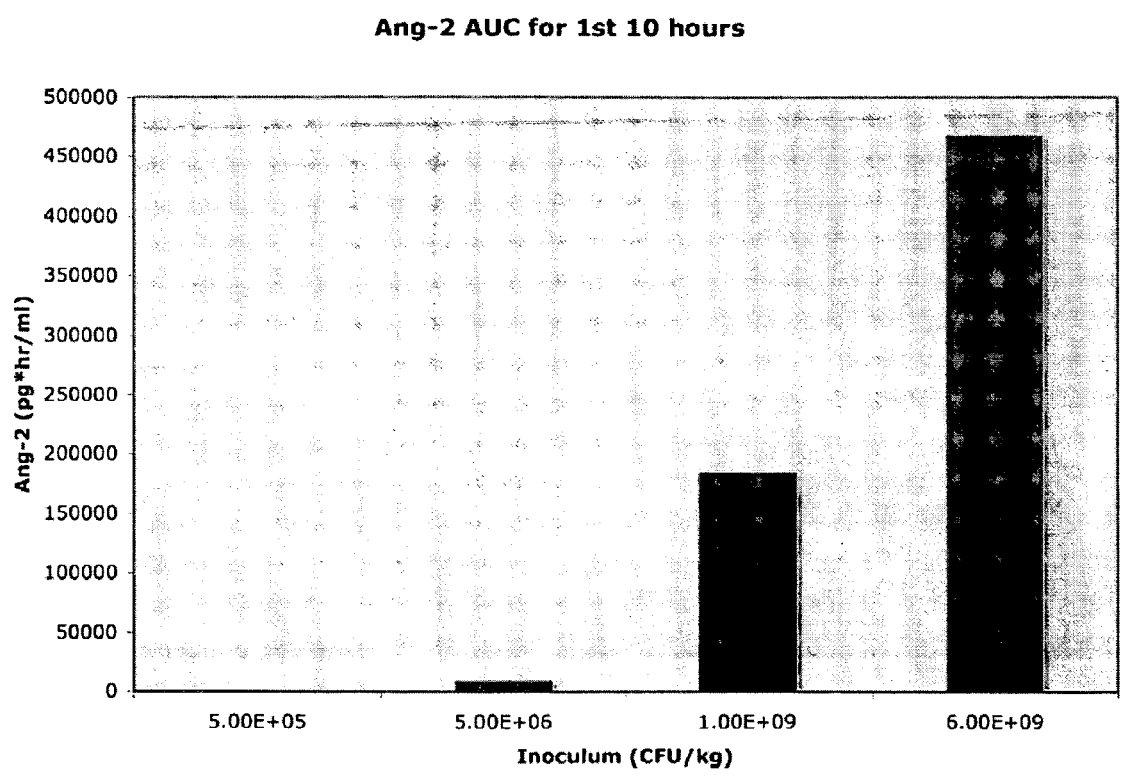
FIG. 7 shows a quantification of the area under the curve for the temporal profiles of Ang-2 elevation (FIGS. 1-4).

The temporal pattern of Ang-2 elevation in each of the animals is shown in FIGS. 1-4. In baboons infected with higher dosages of the bacilli, a rapid rise of Ang-2 in the serum of the animals is observed (FIGS. 1 and 2). At all dosing levels, a rise-plateau-rise shape of the curve across the multiple dosing regimens is observed (FIGS. 5 and 6). To quantify the dose response of Ang-2 to the inoculum, the area under the curve for the temporal profiles of Ang-2 elevation (FIGS. 1-4) was calculated (FIG. 7). The data presented in FIG. 7 demonstrate that Ang-2 elevation is greatest in animals infected with the highest dosages of the bacilli.

Example 2

Pre-Treatment of Baboons with Activated Protein C Before Infection

In this example, we demonstrate that pre-treatment with an activated protein C (e.g., Xigris) before infection with the anthrax bacilli decreases the pathogenicity of the bacilli.

Anthrax bacilli of the Sterne strain of bacilli were infused intravenously into baboons and serial plasma samples were obtained over time (FIG. 8). Each line of FIG. 8 represents results from a single baboon. Two of the animals (represented as lines with filled squares) were treated with $6\times10^9$ CFU/kg of bacilli. Both of these animals subsequently died. Four of the animals (represented as lines with open squares) were pre-treated with activated protein C (Xigris) prior to infection with $6\times10^9$ CFU/kg of bacilli. None of the pre-treated animals died. Two animals (represented as lines with diamonds) were treated with $5\times10^6$ CFU/kg of bacilli with no pre-treatment. Neither of these animals died. These results demonstrate that pre-treatment with activated protein C may decrease the pathogenicity associated with anthrax infection.

Example 3

Ang-2 Release from HUVECs

Human umbilical vein endothelial cells (HUVECs) at 80% confluence were treated with 1 mg/ml lethal toxin (LT), a protein component of the anthrax toxin. Accumulation of Ang-2 was measured in conditioned media by commercial ELISA. Ang-2 measurements were normalized against the protein content of the cell lysate. To enable comparison with von Willebrand factor (vWF, measured by commercial ELISA), values are presented as percentage of negative control (FIG. 9). Both Ang-2 and vWF levels rose shortly after LT treatment. Since vWF is released from Weibel-Palade bodies stored in quiescent endothelial cells, these data suggest that Ang-2 release is mediated by a similar mechanism.

In order to determine the effects of Ang-1 treatment on the LT-induced cell permeability, confluent monolayers of HUVECs were also treated with 1 mg/ml LT with or without 300 ng/ml of Ang-1. Electrical resistance across the monolayer was measured with a hand-held resistance meter to assess the permeability of water through paracellular gaps in the monolayer. As shown in FIG. 10, exposure to LT induces a progressive increase in cell permeability, whereas co-incubation with Ang-1 fortifies the barrier function of the endothelial cells. The results show that Ang-1 reverses LT-mediated cell permeability.

Example 4

Effect of Ang-1 Pretreatment on Lethality of *Bacillus anthracis* Lethal Toxin

The effect of Ang-1 expression on survival after treatment with anthrax LT was tested in a mouse model. 8-week-old C57BL6/J male mice were administered 50 or 100 μg of anthrax LT (LT 50, LT 100 respectively) by tail vein, 48 hours prior to which they were either treated with 0.9% saline intravenously or $10^9$ particles of recombinant adenovirus encoding human Ang-1 suspended in 0.9% saline (Ad-Ang-1, a recombinant adenovirus that is commonly used to induce transient systemic overexpression of the inserted gene). The results shown in FIG. 11 indicate that anthrax LT had a dose-dependent lethality in this model and that Ang-1 pretreatment had a significant protective effect (n=2-4 per animals per group).

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification, including U.S. Provisional Application Ser. Nos. 60/798,639 and 60/716,339, U.S. Ser. No. 11/519,954, and PCT/US2006/035582, are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of treating systemic anthrax infection in a subject, said method comprising the step of administering to said subject an Ang-2 antagonist in an amount sufficient to treat said systemic anthrax infection in said subject.

2. The method of claim 1, wherein said Ang-2 antagonist is selected from the group consisting of: an antibody that specifically binds to Ang-2; an isolated Ang-1 polypeptide or biologically active fragment thereof; an Ang-1 agonist antibody; an Ang-2 binding protein that blocks Ang-2 binding to Tie-2 receptor; a Tie-2 binding protein that specifically blocks Ang-2 binding to Tie-2; a soluble Tie-2 fragment that specifically binds to Ang-2; a dominant active mutant of Tie-2; an antibody that specifically binds to Tie-2 and selectively inhibits Ang-2 binding to Tie-2; an inhibitor of MLC phosphorylation; an activator of pI90RhoGAP activity; an inhibitor of RhoGTPase activity; and an inhibitor of Rho kinase activity.

3. The method claim 2, wherein said Ang-2 antagonist is a purified antibody, or fragment thereof, that specifically binds to Ang-2.

4. The method of claim 3, wherein said monoclonal antibody is LI-7(N) or an antigen-binding fragment or derivative thereof.

5. The method of claim 4, wherein said L 1-7(N) is a chimeric, humanized, or fully human L 1-7(N) antibody.

6. The method of claim 2, wherein said Ang-2 antagonist is an isolated Ang-1 polypeptide, or biologically active fragment thereof, or an Ang-1 agonist antibody.

7. The method of claim 1, further comprising administering an antibiotic.

8. The method of claim 7, wherein said antibiotic is ciprofloxacin, doxycycline, erythromycin, vancomycin, or penicillin.

9. The method of claim 1, further comprising administering activated protein C.

10. The method of claim 9, wherein said activated protein C is drotrecogin alpha.

11. A method of treating, inhibiting, or preventing systemic anthrax infection in a subject, said method comprising the step of administering to said subject an Ang-2 antagonist in an amount sufficient to treat, inhibit, or prevent said systemic anthrax infection in said subject, wherein said Ang-2 antagonist is administered to the subject within two days after said subject is infected with anthrax bacilli.

12. The method of claim 11, wherein said Ang-2 antagonist is administered to the subject within one day after said subject is infected with anthrax bacilli.

13. The method of claim 1, wherein said Ang-2 antagonist is administered intravenously.

14. The method of claim 1, further comprising monitoring said systemic anthrax infection in said subject, wherein said monitoring comprises measuring the level of Ang-2 polypeptide in a sample from said subject.

15. The method of claim 14, wherein said monitoring is used to determine the therapeutic dosage of said Ang-2 antagonist.

* * * * *

SEQUENCE LISTING

<160> NUMBER OF SEQ ID NOS: 4

<210> SEQ ID NO 1
<211> LENGTH: 496
<212> TYPE: PRT
<213> ORGANISM: Homo sapiens

<400> SEQUENCE: 1

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160
```

```
Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

<210> SEQ ID NO 2
<211> LENGTH: 4338
<212> TYPE: DNA
<213> ORGANISM: Homo sapiens

<400> SEQUENCE: 2
ggggcacact catgcattcc tgtcaagtca tcttgtgaaa ggctgcctgc ttccagcttg      60
gcttggatgt gcaaccttaa taaaactcac tgaggtctgg gagaaaatag cagatctgca    120
gcagataggg tagaggaaag ggtctagaat atgtacacgc agctgactca ggcaggctcc    180
atgctgaacg gtcacacaga gaggaaacaa taaatctcag ctactatgca ataaatatct    240
caagttttaa cgaagaaaaa catcattgca gtgaaataaa aaattttaaa attttagaac    300
```

```
aaagctaaca aatggctagt tttctatgat tcttcttcaa acgctttctt tgaggggggaa    360 agagtcaaac aaacaagcag ttttacctga aataaagaac tagttttaga ggtcagaaga    420
aaggagcaag ttttgcgaga ggcacggaag gagtgtgctg gcagtacaat gacagttttc    480 cttttcctttg cttttcctcgc tgccattctg actcacatag ggtgcagcaa tcagcgccga    540
agtccagaaa acagtgggag aagatataac cggattcaac atgggcaatg tgcctacact    600
ttcattcttc cagaacacga tggcaactgt cgtgagagta cgacagacca gtacaacaca    660
aacgctctgc agagagatgc tccacacgtg gaaccggatt tctcttccca gaaacttcaa    720
catctggaac atgtgatgga aaattatact cagtggctgc aaaaacttga gaattacatt    780
gtggaaaaca tgaagtcgga gatggcccag atacagcaga atgcagttca gaaccacacg    840
gctaccatgc tggagatagg aaccagcctc ctctctcaga ctgcagagca gaccagaaag    900
ctgacagatg ttgagaccca ggtactaaat caaacttctc gacttgagat acagctgctg    960
gagaattcat tatccaccta caagctagag aagcaacttc ttcaacgac aaatgaaatc   1020 ttgaagatcc atgaaaaaaa cagtttatta gaacataaaa tcttagaaat ggaaggaaaa   1080
cacaaggaag agttggacac cttaaaggaa gagaaagaga accttcaagg cttggttact   1140
cgtcaaacat atataatcca ggagctggaa aagcaattaa acagagctac caccaacaac   1200
agtgtccttc agaagcagca actggagctg atggacacag tccacaacct tgtcaatctt   1260
tgcactaaag aaggtgtttt actaagggga ggaaaaagag aggaagagaa accatttaga   1320
gactgtgcag atgtatatca agctggtttt aataaaagtg gaatctacac tatttatatt   1380
aataatatgc cagaacccaa aaaggtgttt tgcaatatgg atgtcaatgg gggaggttgg   1440
actgtaatac aacatcgtga agatggaagt ctagatttcc aaagaggctg gaaggaatat   1500
aaaatgggtt ttggaaatcc ctccggtgaa tattggctgg ggaatgagtt tattttttgcc   1560 attaccagtc agaggcagta catgctaaga attgagttaa tggactggga agggaaccga   1620
gcctattcac agtatgacag attccacata ggaaatgaaa agcaaaacta taggttgtat   1680
ttaaaaggtc acactgggac agcaggaaaa cagagcagcc tgatcttaca cggtgctgat   1740
ttcagcacta aagatgctga taatgacaac tgtatgtgca aatgtgccct catgttaaca   1800
ggaggatggt ggtttgatgc ttgtggcccc tccaatctaa atggaatgtt ctatactgcg   1860
ggacaaaacc atggaaaact gaatgggata aagtggcact acttcaaagg gcccagttac   1920
tccttacgtt ccacaactat gatgattcga ccttttagatt tttgaaagcg caatgtcaga   1980
agcgattatg aaagcaacaa agaaatccgg agaagctgcc aggtgagaaa ctgtttgaaa   2040
acttcagaag caaacaatat tgtctcccctt ccagcaataa gtggtagtta tgtgaagtca   2100
ccaaggttct tgaccgtgaa tctggagccg tttgagttca aagagtctc tacttggggt   2160 gacagtgctc acgtggctcg actatagaaa actccactga ctgtcgggct ttaaaaaggg   2220
aagaaactgc tgagcttgct gtgcttcaaa ctactactgg accttatttt ggaactatgg   2280
tagccagatg ataaatatgg ttaatttcat gtaaaacaga aaaaagagt gaaaagaga   2340 atatacatga agaatagaaa caagcctgcc ataatccttt ggaaaagatg tattatacca   2400
gtgaaaaggt gttatatcta tgcaaaccta ctaacaaatt atactgttgc acaattttga   2460
taaaaattta gaacagcatt gtcctctgag ttggttaaat gttaatggat ttcagaagcc   2520
taattccagt atcatactta ctagttgatt tctgcttacc catcttcaaa tgaaaattcc   2580 attttttgtaa gccataatga actgtagtac atggacaata agtgtgtggt agaaacaaac   2640
tccattactc tgattttga tacagttttc agaaaaagaa atgaacataa tcaagtaagg   2700
```

-continued

```
atgtatgtgg tgaaaactta ccacccccat actatggttt tcatttactc taaaaactga   2760
ttgaatgata tataaatata tttatagcct gagtaaagtt aaaagaatgt aaaatatatc   2820
atcaagttct taaaataata tacatgcatt taatatttcc tttgatatta tacaggaaag   2880
caatattttg gagtatgtta agttgaagta aaagcaagta ctctggagca gttcatttta   2940
cagtatctac ttgcatgtgt atacatacat gtaacttcat tattttaaaa atatttttag   3000
aactccaata ctcaccctgt tatgtcttgc taatttaaat tttgctaatt aactgaaaca   3060
tgcttaccag attcacactg ttccagtgtc tataaaagaa acactttgaa gtctataaaa   3120
aataaaataa ttataaatat cattgtacat agcatgttta tatctgcaaa aaacctaata   3180
gctaattaat ctggaatatg caacattgtc cttaattgat gcaaataaca caatgctca    3240 aagaaatcta ctatatccct taatgaaata catcattctt catatatttc tccttcagtc   3300 cattcccta  ggcaattttt aatttttaaa aattattatc aggggagaaa aattggcaaa   3360
actattatat gtaagggaaa tatatacaaa aagaaaatta atcatagtca cctgactaag   3420
aaattctgac tgctagttgc cataaataac tcaatggaaa tattcctatg ggataatgta   3480
ttttaagtga attttggggg tgcttgaagt tactgcatta ttttatcaag aagtcttctc   3540
tgcctgtaag tgtccaaggt tatgacagta acagttttt  attaaaacat gagtcactat   3600
gggatgagaa aattgaaata aagctactgg gcctcctctc ataaaagaga cagttgttgg   3660
caaggtagca ataccagttt caaacttggt gacttgatcc actatgcctt aatggtttcc   3720
tccatttgag aaaataaagc tattcacatt gttaagaaaa atacttttta agtttacca    3780 tcaagtcttt tttatattta tgtgtctgta ttctacccct ttttgcctta caagtgatat   3840
ttgcaggtat tataccattt ttctattctt ggtggcttct tcatagcagg taagcctctc   3900
cttctaaaaa cttctcaact gttttcattt aagggaaaga aaatgagtat tttgtccttt   3960
tgtgttccta cagacacttt cttaaaccag tttttggata agaatacta tttccaaact    4020 catattacaa aaacaaaata aaataataaa aaaagaaagc atgatattta ctgttttgtt   4080
gtctgggttt gagaaatgaa atattgtttc caattattta taataaatca gtataaaatg   4140
ttttatgatt gttatgtgta ttatgtaata cgtacatgtt tatggcaatt taacatgtgt   4200 attctttaa  ttgtttcaga ataggataat taggtattcg aattttgtct ttaaaattca   4260
tgtggtttct atgcaaagtt cttcatatca tcacaacatt atttgattta aataaaattg   4320
aaagtaatat ttgtgcaa                                                 4338
```

<210> SEQ ID NO 3
<211> LENGTH: 496
<212> TYPE: PRT
<213> ORGANISM: Homo sapiens

<400> SEQUENCE: 3

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80
```

```
Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

<210> SEQ ID NO 4

<211> LENGTH: 2269
<212> TYPE: DNA
<213> ORGANISM: Homo sapiens

<400> SEQUENCE: 4

| | | | | | |
|---|---|---|---|---|---|
| tgggttggtg | tttatctcct | cccagccttg | agggagggaa | caacactgta | ggatctgggg | 60 |
| agagaggaac | aaaggaccgt | gaaagctgct | ctgtaaaagc | tgacacagcc | ctcccaagtg | 120 |
| agcaggactg | ttcttcccac | tgcaatctga | cagtttactg | catgcctgga | gagaacacag | 180 |
| cagtaaaaac | caggtttgct | actggaaaaa | gaggaaagag | aagactttca | ttgacggacc | 240 |
| cagccatggc | agcgtagcag | ccctgcgttt | cagacggcag | cagctcggga | ctctggacgt | 300 |
| gtgtttgccc | tcaagtttgc | taagctgctg | gtttattact | gaagaaagaa | tgtggcagat | 360 |
| tgttttcttt | actctgagct | gtgatcttgt | cttggccgca | gcctataaca | actttcggaa | 420 |
| gagcatggac | agcataggaa | agaagcaata | tcaggtccag | catgggtcct | gcagctacac | 480 |
| tttcctcctg | ccagagatgg | acaactgccg | ctcttcctcc | agcccctacg | tgtccaatgc | 540 |
| tgtgcagagg | gacgcgccgc | tcgaatacga | tgactcggtg | cagaggctgc | aagtgctgga | 600 |
| gaacatcatg | gaaaacaaca | ctcagtggct | aatgaagctt | gagaattata | tccaggacaa | 660 |
| catgaagaaa | gaaatggtag | agatacagca | gaatgcagta | cagaaccaga | cggctgtgat | 720 |
| gatagaaata | gggacaaacc | tgttgaacca | aacagctgag | caaacgcgga | agttaactga | 780 |
| tgtggaagcc | caagtattaa | atcagaccac | gagacttgaa | cttcagctct | tggaacactc | 840 |
| cctctcgaca | aacaaattgg | aaaaacagat | tttggaccag | accagtgaaa | taaacaaatt | 900 |
| gcaagataag | aacagtttcc | tagaaaagaa | ggtgctagct | atggaagaca | agcacatcat | 960 |
| ccaactacag | tcaataaaag | aagagaaaga | tcagctacag | gtgttagtat | ccaagcaaaa | 1020 |
| ttccatcatt | gaagaactag | aaaaaaaaat | agtgactgcc | acggtgaata | attcagttct | 1080 |
| tcaaaagcag | caacatgatc | tcatggagac | agttaataac | ttactgacta | tgatgtccac | 1140 |
| atcaaactca | gctaaggacc | ccactgttgc | taaagaagaa | caaatcagct | tcagagactg | 1200 |
| tgctgaagta | ttcaaatcag | gacacaccac | aaatggcatc | tacacgttaa | cattccctaa | 1260 |
| ttctacagaa | gagatcaagg | cctactgtga | catggaagct | ggaggaggcg | ggtggacaat | 1320 |
| tattcagcga | cgtgaggatg | gcagcgttga | ttttcagagg | acttggaaag | aatataaagt | 1380 |
| gggatttggt | aacccttcag | gagaatattg | gctgggaaat | gagtttgttt | cgcaactgac | 1440 |
| taatcagcaa | cgctatgtgc | ttaaaataca | ccttaaagac | tgggaaggga | atgaggctta | 1500 |
| ctcattgtat | gaacatttct | atctctcaag | tgaagaactc | aattataggo | ttcaccttaa | 1560 |
| aggacttaca | gggacagccg | gcaaaataag | cagcatcagc | caaccaggaa | atgattttag | 1620 |
| cacaaaggat | ggagacaacg | acaaatgtat | ttgcaaatgt | tcacaaatgc | taacaggagg | 1680 |
| ctggtggttt | gatgcatgtg | gtccttccaa | cttgaacgga | atgtactatc | cacagaggca | 1740 |
| gaacacaaat | aagttcaacg | gcattaaatg | gtactactgg | aaaggctcag | gctattcgct | 1800 |
| caaggccaca | accatgatga | tccgaccagc | agatttctaa | acatcccagt | ccacctgagg | 1860 |
| aactgtctcg | aactattttc | aaagacttaa | gcccagtgca | ctgaaagtca | cggctgcgca | 1920 |
| ctgtgtcctc | ttccaccaca | gagggcgtgt | gctcggtgct | gacgggaccc | acatgctcca | 1980 |
| gattagagcc | tgtaaacttt | atcacttaaa | cttgcatcac | ttaacggacc | aaagcaagac | 2040 |
| cctaaacatc | cataattgtg | attagacaga | acacctatgc | aaagatgaac | ccgaggctga | 2100 |
| gaatcagact | gacagtttac | agacgctgct | gtcacaacca | agaatgttat | gtgcaagttt | 2160 |

-continued

```
atcagtaaat aactggaaaa cagaacactt atgttataca atacagatca tcttggaact   2220
gcattcttct gagcactgtt tatacactgt gtaaataccc atatgtcct               2269
```